United States Patent
Yoon et al.

(10) Patent No.: US 9,951,226 B2
(45) Date of Patent: Apr. 24, 2018

(54) COMPOUND BASED ON CYANINE SCAFFOLD FOR DIAGNOSIS SEPSIS BY SELECTIVELY DETECT GLUTATHIONE

(71) Applicant: EWHA UNIVERSITY—INDUSTRY COLLABORATION FOUNDATION, Seoul (KR)

(72) Inventors: Juyoung Yoon, Seoul (KR); Jun Yin, Seoul (KR); Gyoungmi Kim, Seoul (KR); Dabin Kim, Gyeonggi-do (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 420 days.

(21) Appl. No.: 14/663,990

(22) Filed: Mar. 20, 2015

(65) Prior Publication Data

US 2016/0083344 A1    Mar. 24, 2016

(30) Foreign Application Priority Data

Sep. 24, 2014 (KR) .................. 10-2014-0127887
Mar. 19, 2015 (KR) .................. 10-2015-0038035

(51) Int. Cl.
| | | |
|---|---|---|
| *C09B 23/01* | (2006.01) | |
| *C07D 209/14* | (2006.01) | |
| *G01N 33/68* | (2006.01) | |
| *C07D 401/14* | (2006.01) | |

(52) U.S. Cl.
CPC ........ *C09B 23/0066* (2013.01); *C07D 209/14* (2013.01); *C07D 401/14* (2013.01); *G01N 33/6815* (2013.01); *G01N 2800/26* (2013.01)

(58) Field of Classification Search
CPC .................................................. C09B 23/0066
USPC ........................................... 548/416; 435/6.1
See application file for complete search history.

(56) References Cited

PUBLICATIONS

Yin et al. (JACS, Mar. 2014, 136, 5351-5358).*
Guo et al., "A Fast Response Highly Selective Probe for the Detection of Glutathione in Human Blood Plasma", Sensors, vol. 12, pp. 5940-5950, (2012).
Herzenberg et al., "Glutathione deficiency is associated with impaired survival in HIV disease", Proc. Natl. Acad. Sci. USA, vol. 94, pp. 1967-1972, (1997).
Niu et al., "BODIPY—Based Ratiometric Fluorescent Sensor for Highly Selective Detection of Glutathione over Cysteine and Homocysteine", J. Am. Chem. Soc., vol. 134, pp. 18928-18931, (2012).

(Continued)

*Primary Examiner* — Jezia Riley
(74) *Attorney, Agent, or Firm* — Vorys, Sater, Seymour & Pease LLP; Mih Suhn Koh

(57) ABSTRACT

The present invention relates to a compound based on cyanine scaffold for diagnosing sepsis by selectively detecting glutathione. The compound based on cyanine scaffold according to the present invention has the advantages of maintaining its structure in intracellular environment and of reacting selectively to glutathione only among many amino acids containing thiol group (R—SH) such as cysteine, homocysteine, and glutathione, to produce changes in absorption or fluorescence spectrum, making the compound useful for the detection of in vivo glutathione in biosamples and also for the diagnosis of sepsis characteristically displaying the changes of glutathione concentration.

9 Claims, 26 Drawing Sheets

(56) References Cited

PUBLICATIONS

Shao et al., "Design of Bis-spiropyran Ligands as Dipolar Molecule Receptors and Application to in Vivo Gluthathione Fluorescent Probes", J. Am. Chem. Soc., vol. 132, No. 2, pp. 725-736, (2010).
Wood et al., "Structure, mechanism and regulation of peroxiredoxins", TRENDS in Biochemical Sciences, vol. 28, No. 1, pp. 32-40, (2003).
Yin et al., "Progress on Fluorescent Probes for Thiols", Chin J Anal Chem, vol. 37, Issue 7, pp. 1073-1081, (2009).

* cited by examiner

[Figure 1]
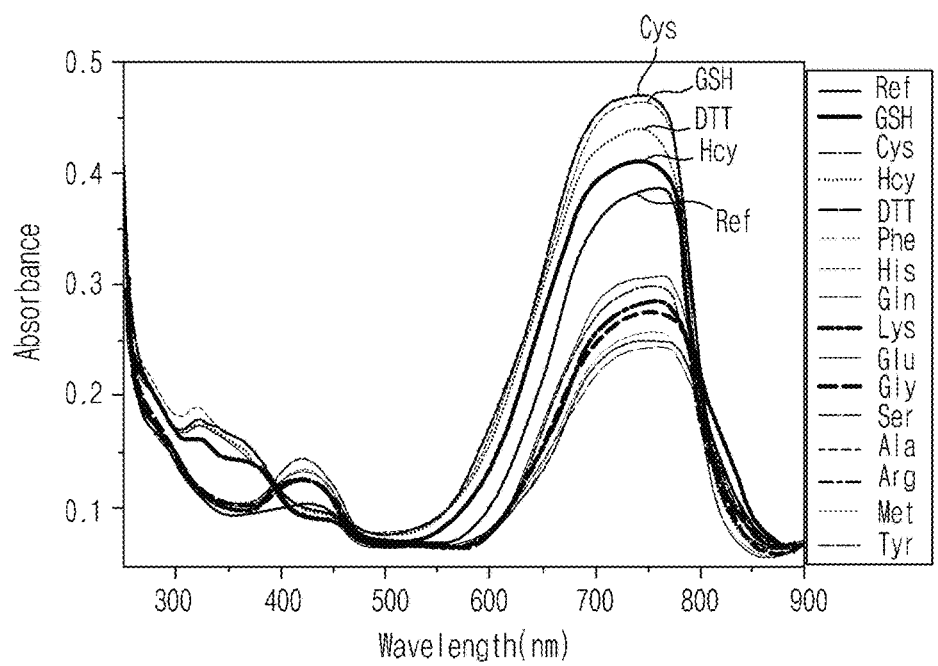

[Figure 2]
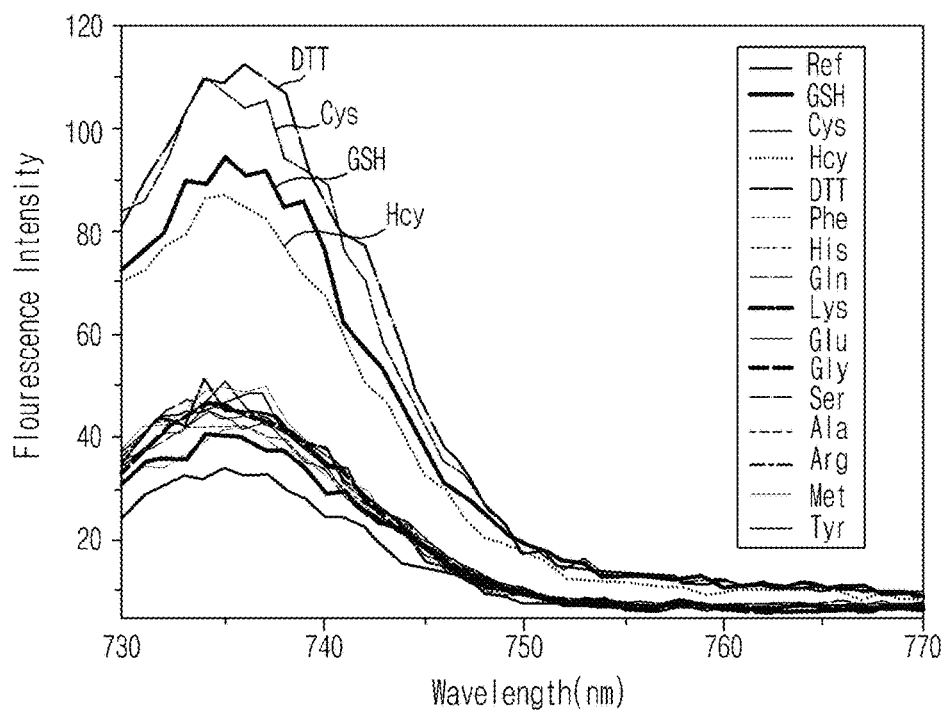

[Figure 3]
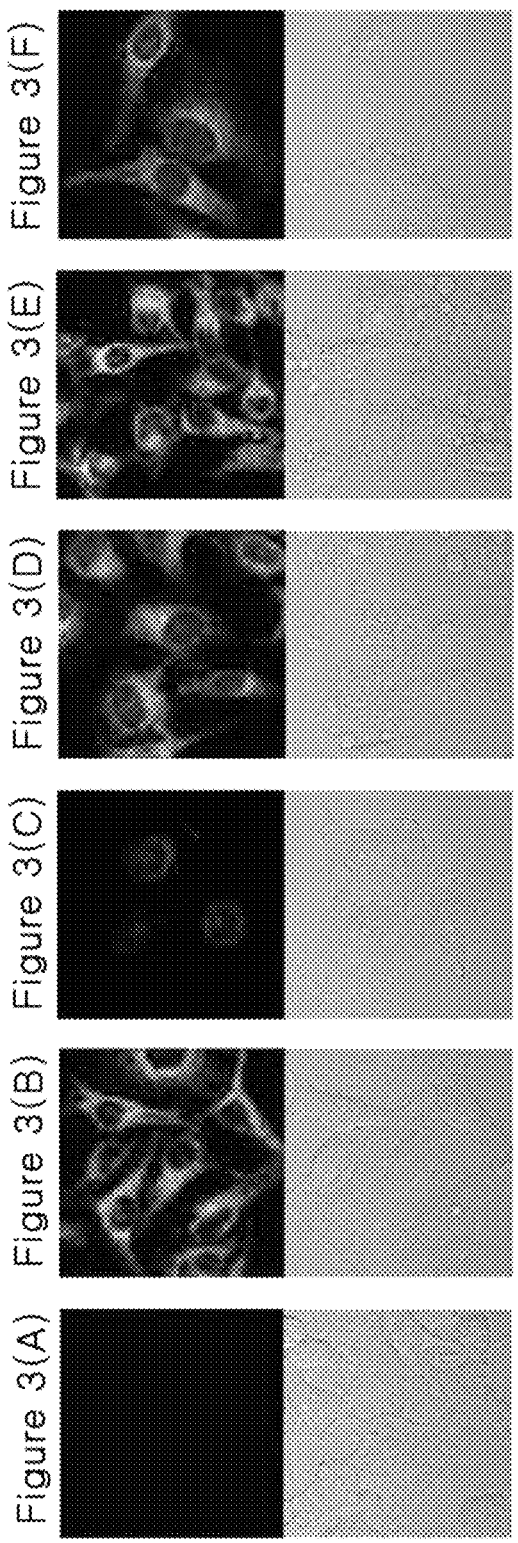

[Figure 4]
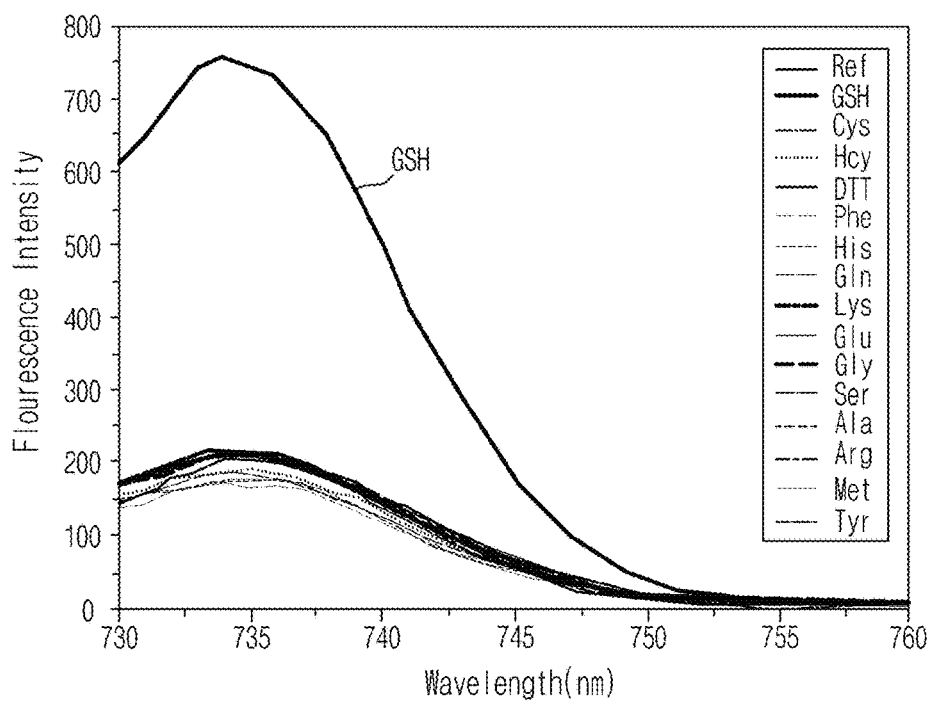

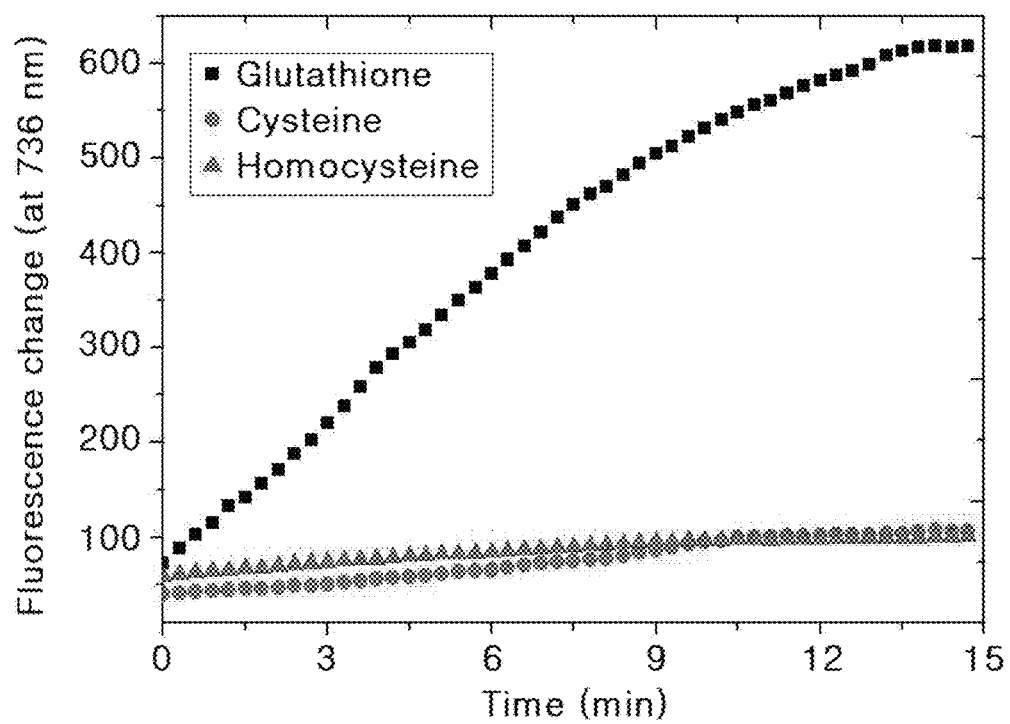
[Figure 5]

[Figure 6]
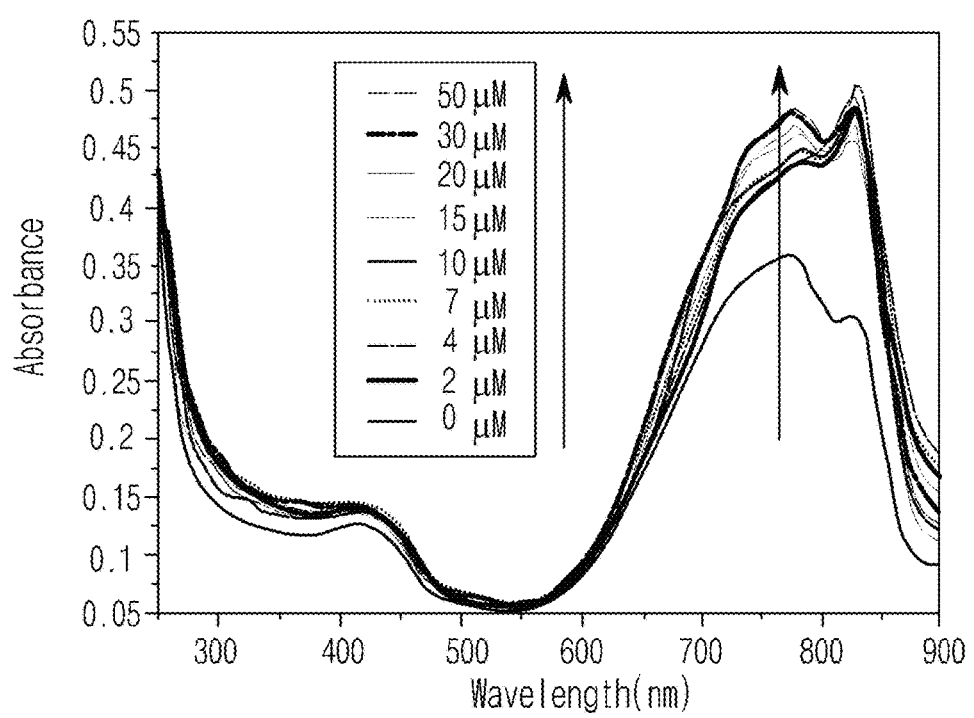

[Figure 7]
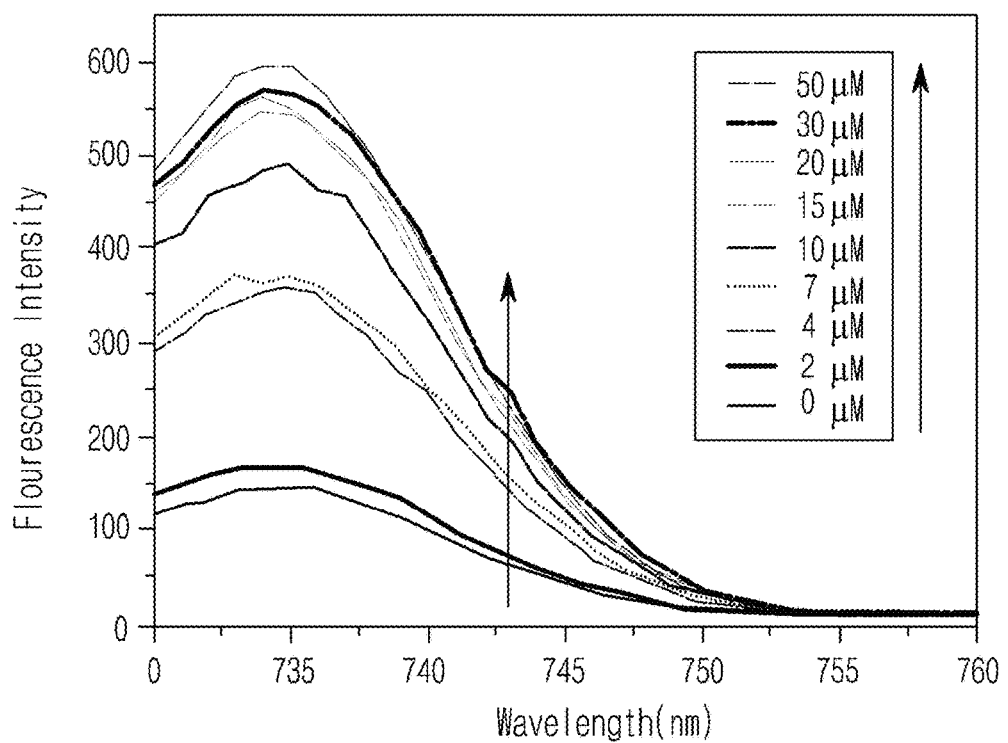

[Figure 8]
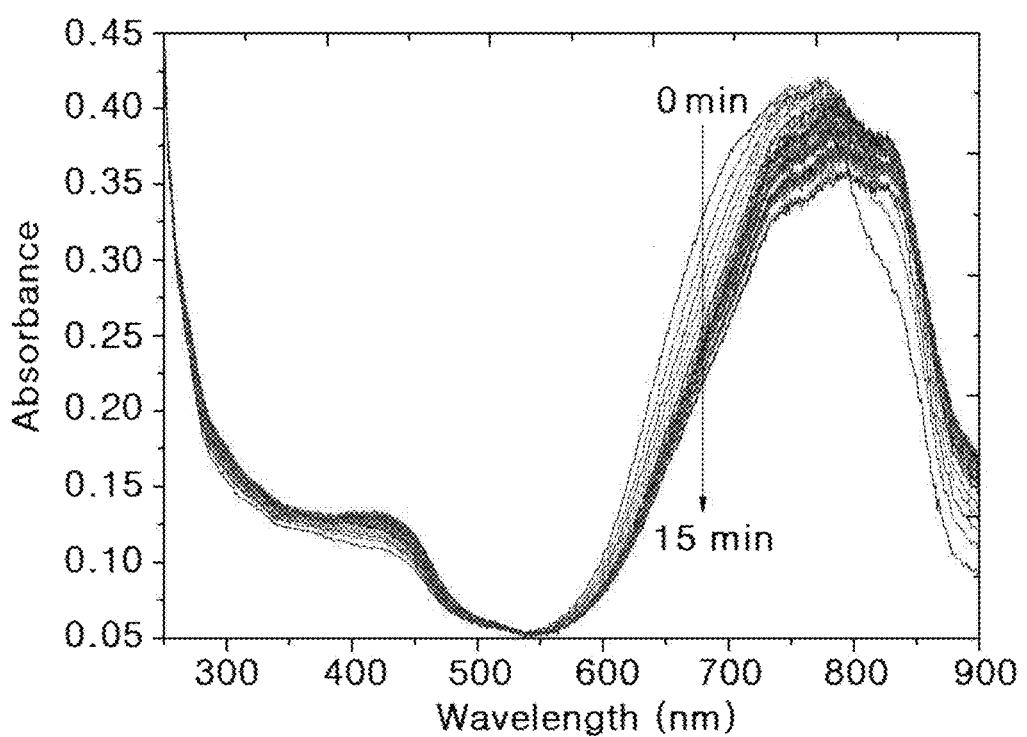

[Figure 9]
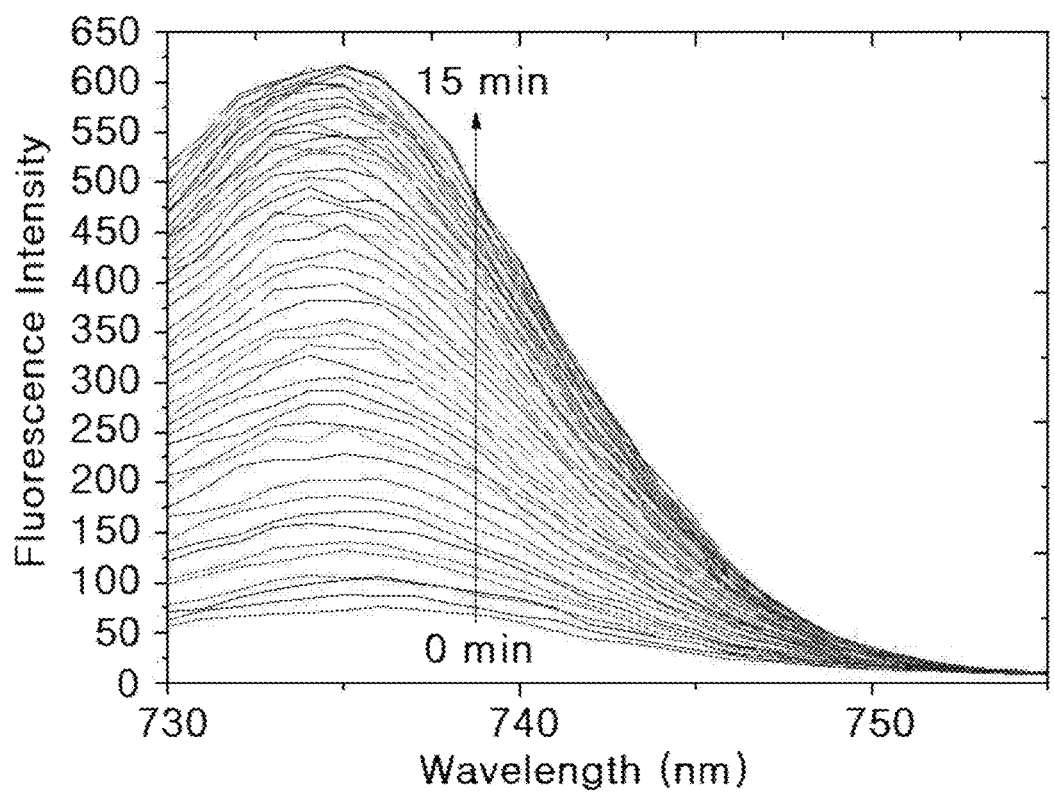

[Figure 10]
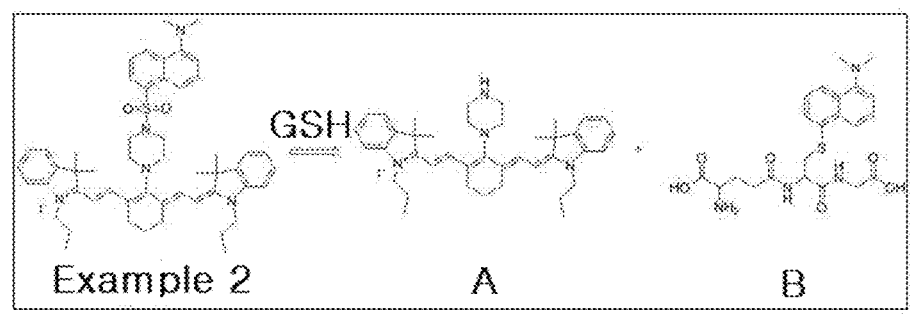
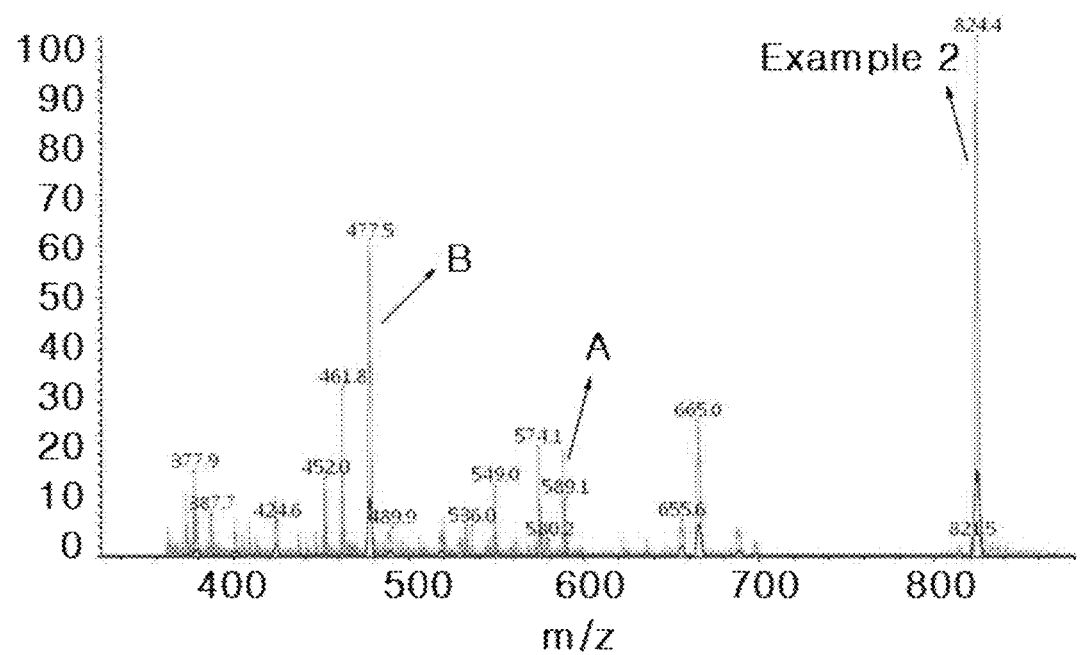

[Figure 11]
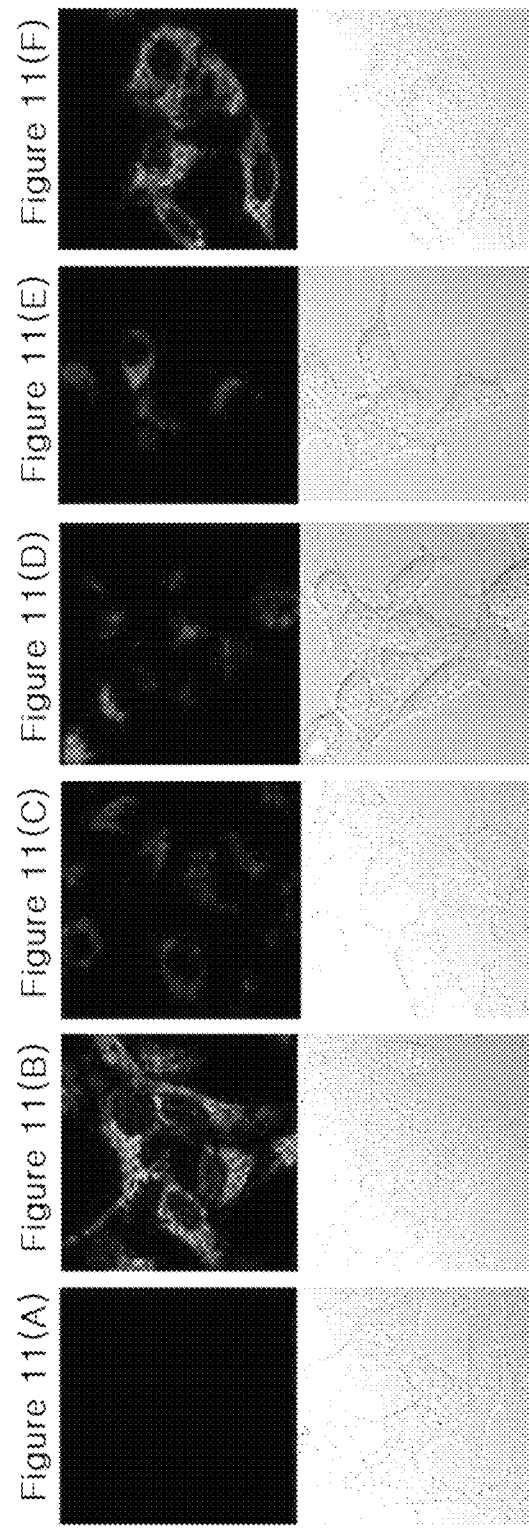

[Figure 14]
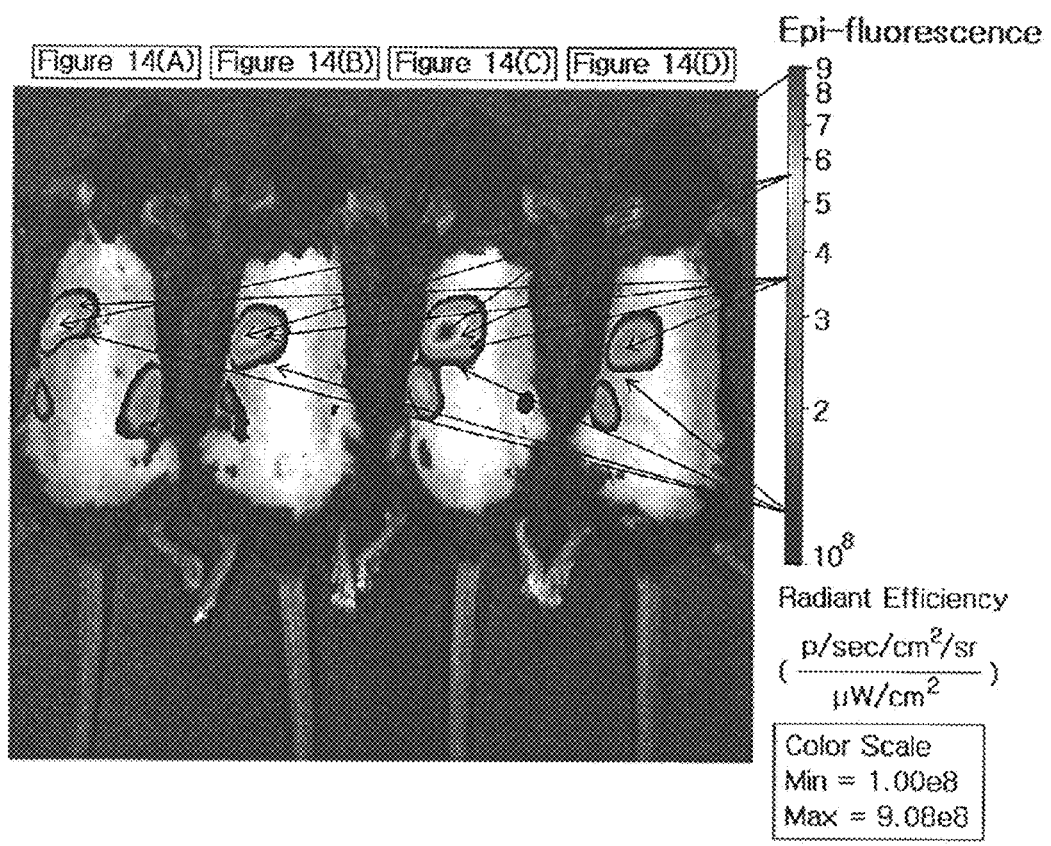

[Figure 15]
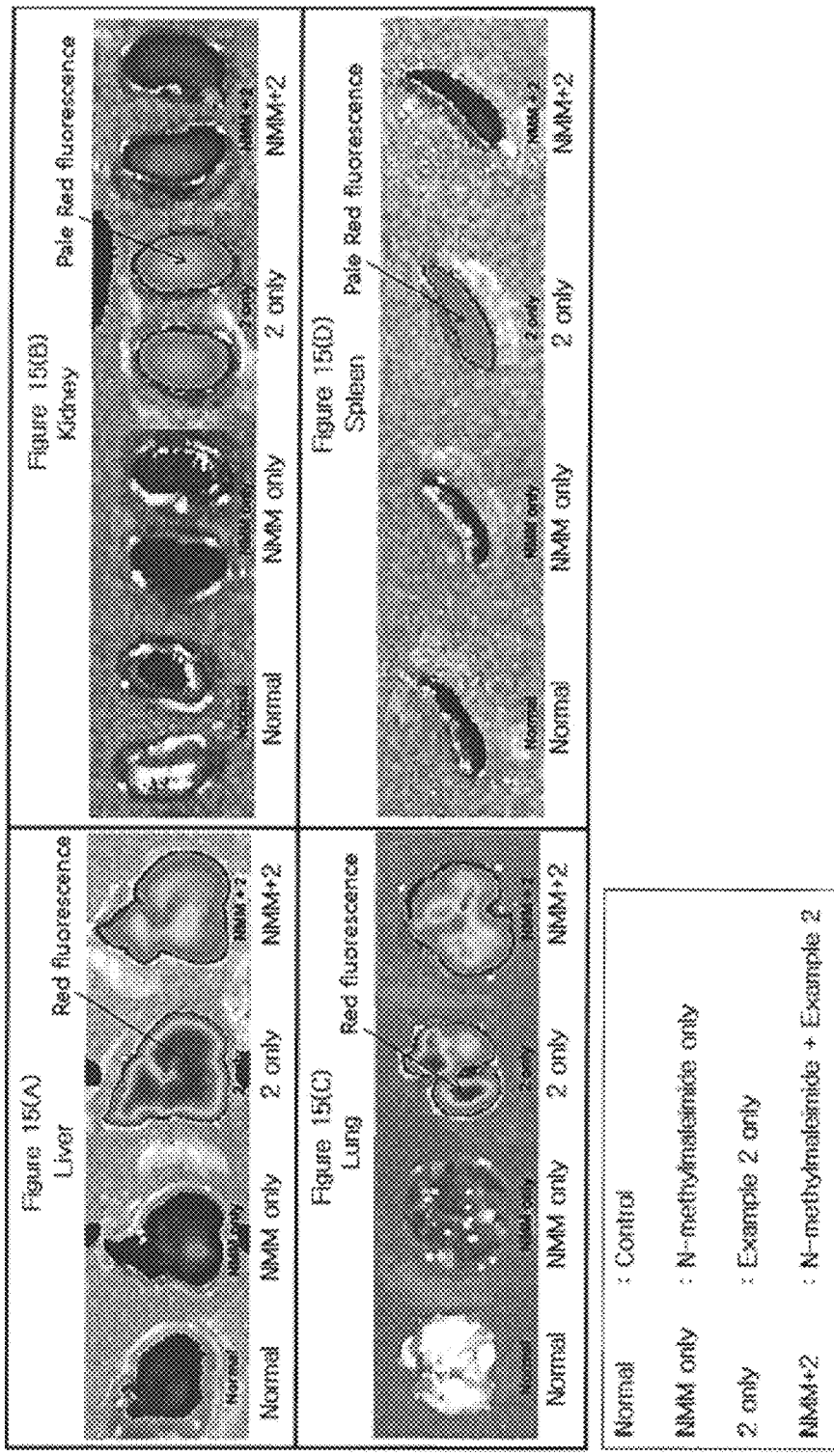

[Figure 16]
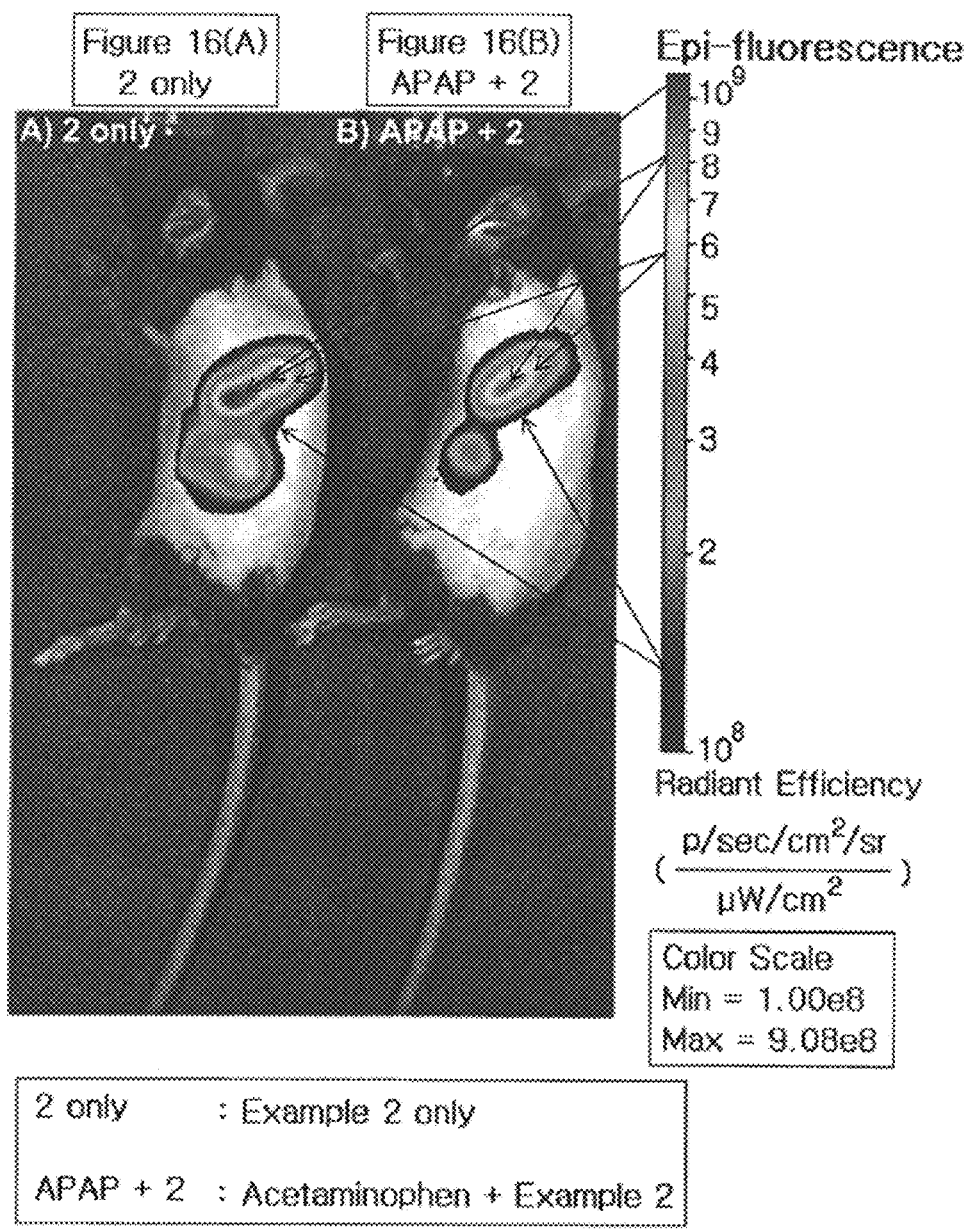

[Figure 17]
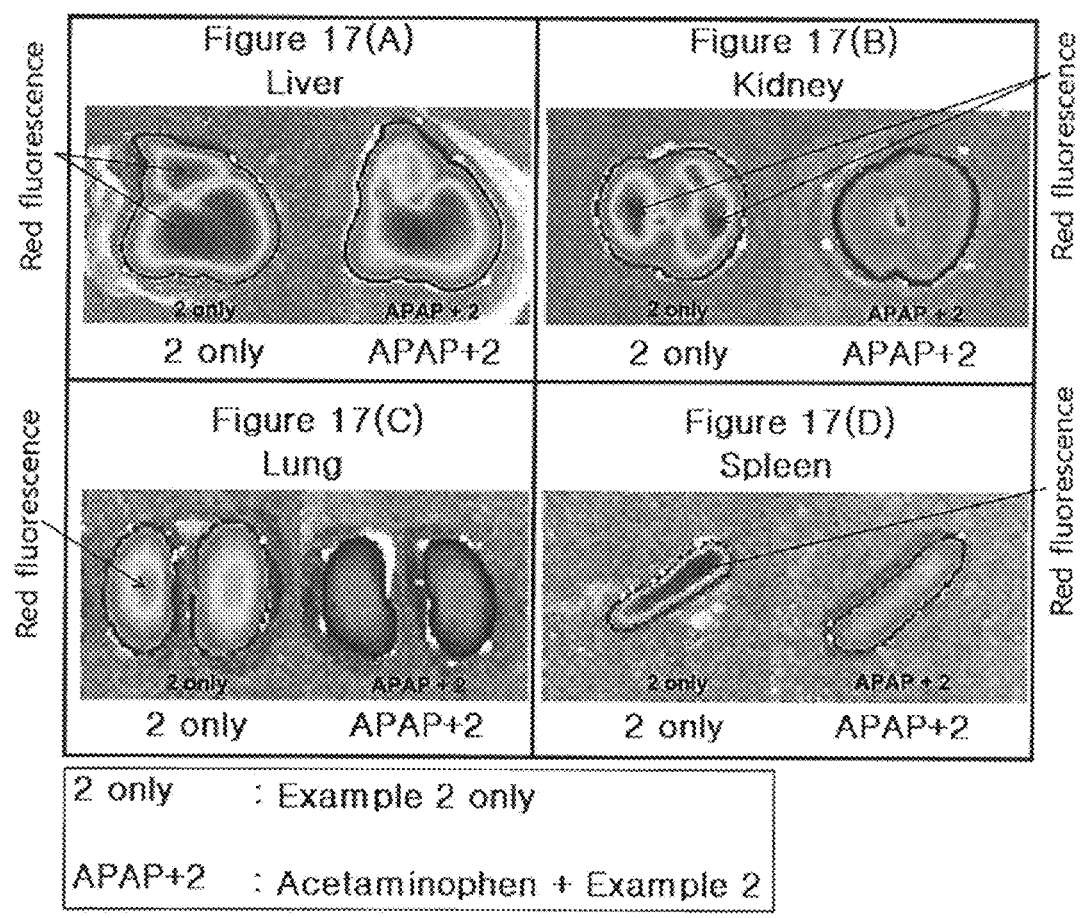

[Figure 18]
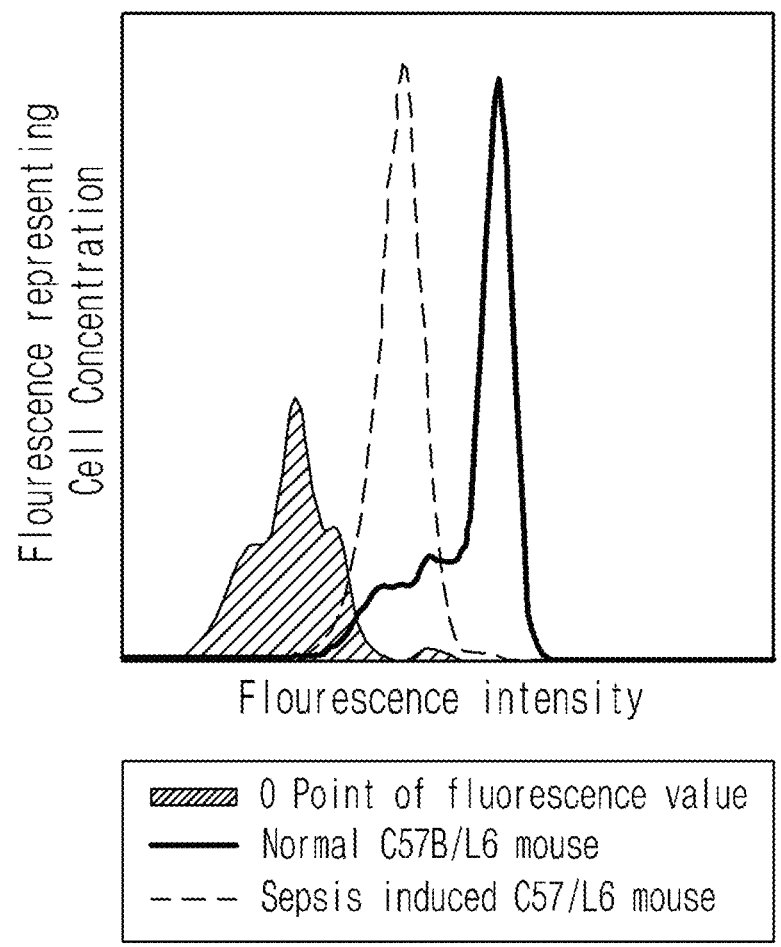

[Figure 19]

| | (A) Differential Interference Channel | (B) Red Fluorescence Channel (575–675 nm) | (C) Green Fluorescence Channel (490–540 nm) | (A)+(B)+(C) Channel |
|---|---|---|---|---|
| Control | | | | |
| Green Fluorescent Protein tagged Pseudomonas Aeruginosa 01 | | | | |
| Example 2 | | | | |
| Green Fluorescent Protein tagged Pseudomonas Aeruginosa 01 + Example 2 | | | | |

[Figure 20]
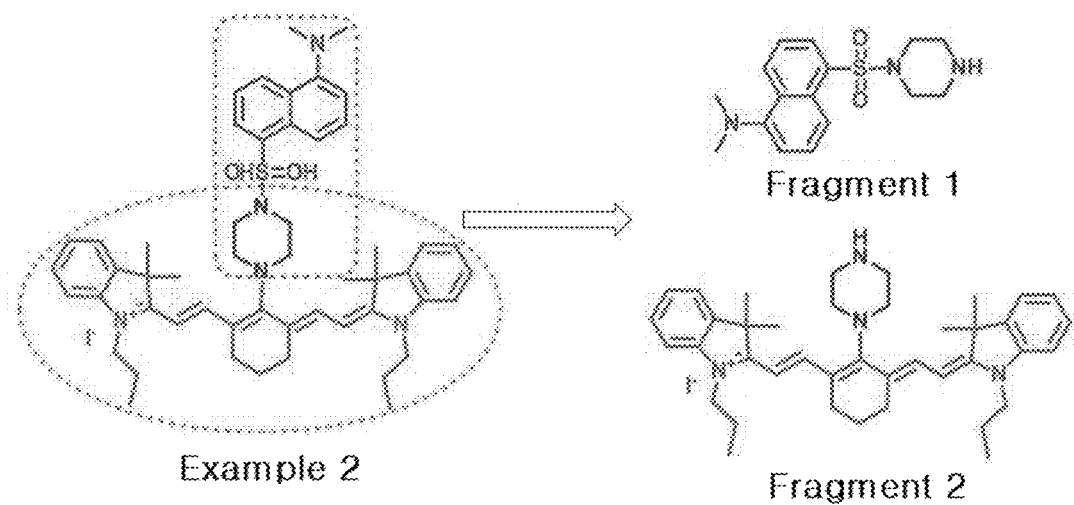

[Figure 21]
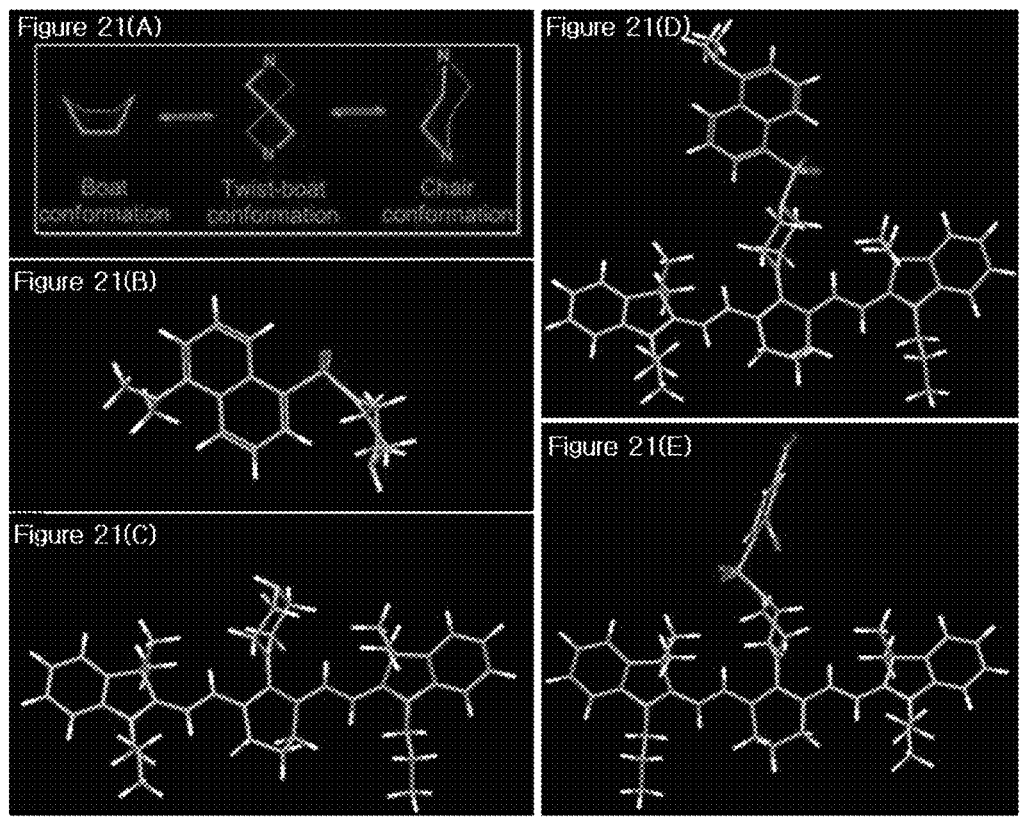

[Figure 22]
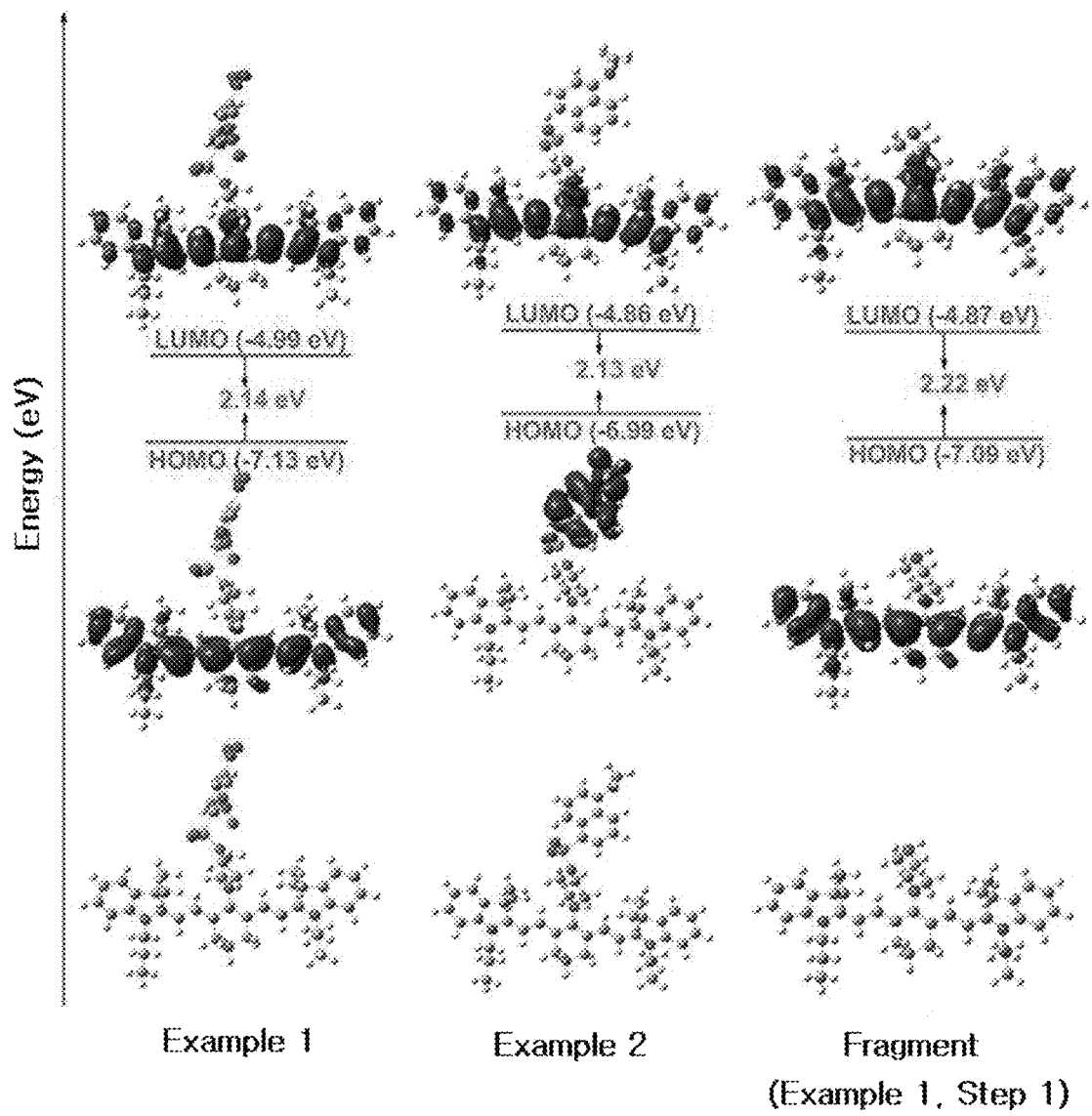

[Figure 23]
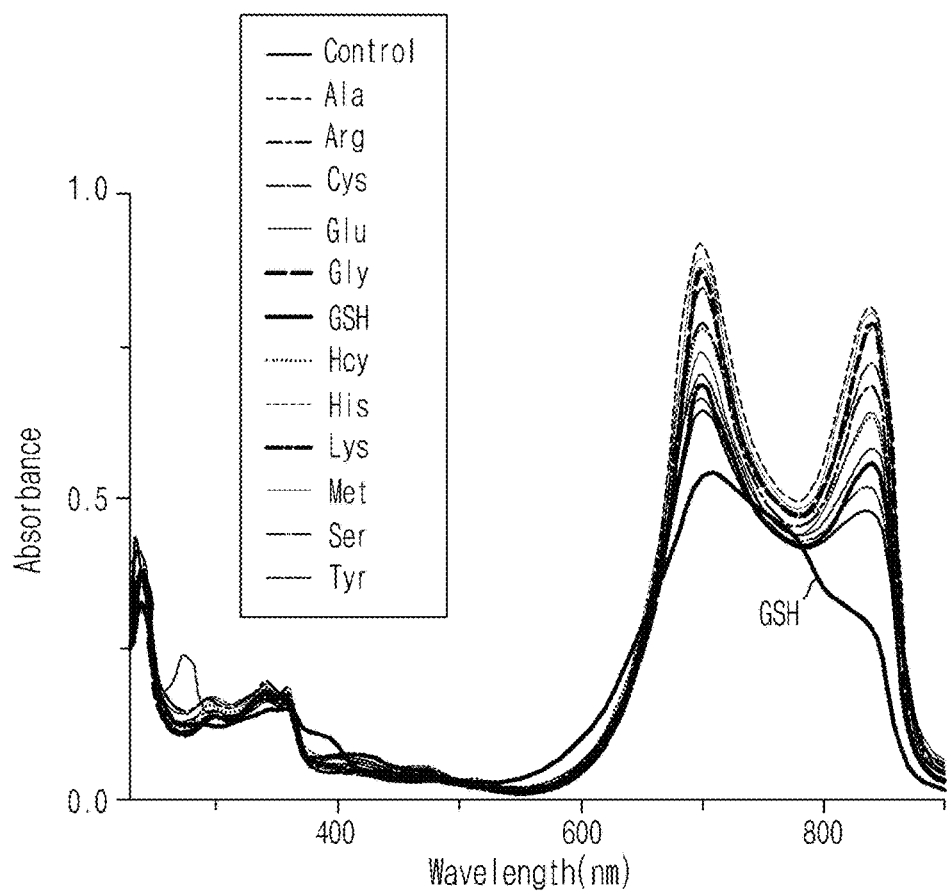

[Figure 24]
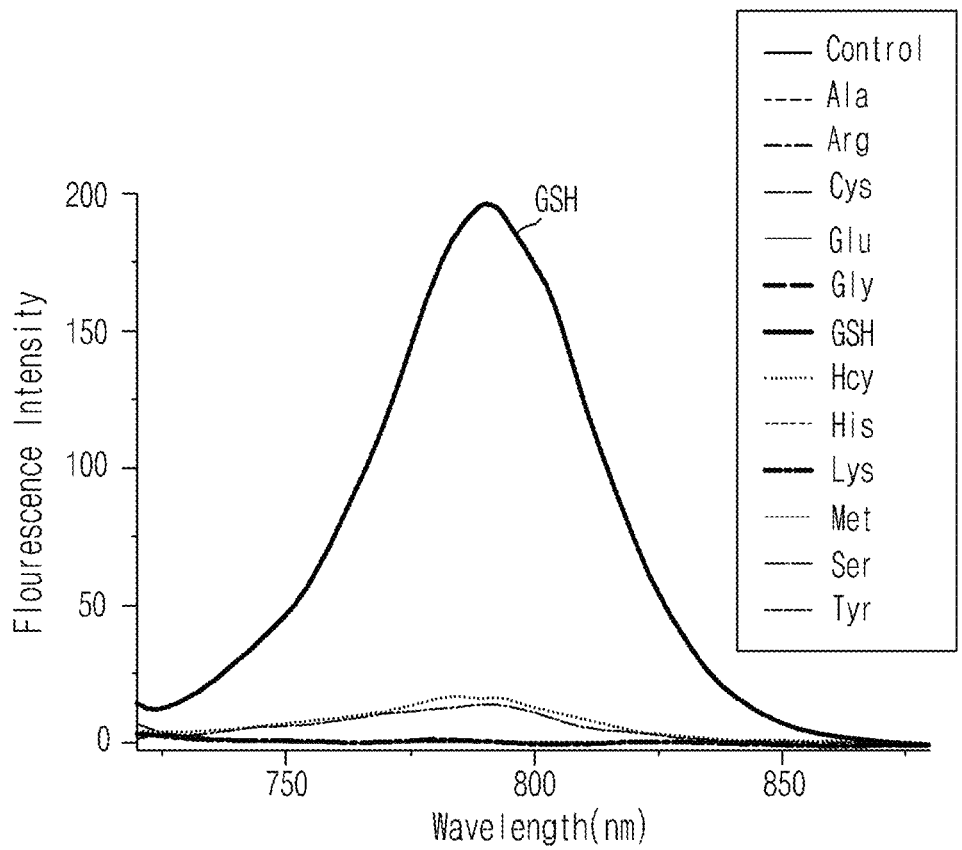

[Figure 25]
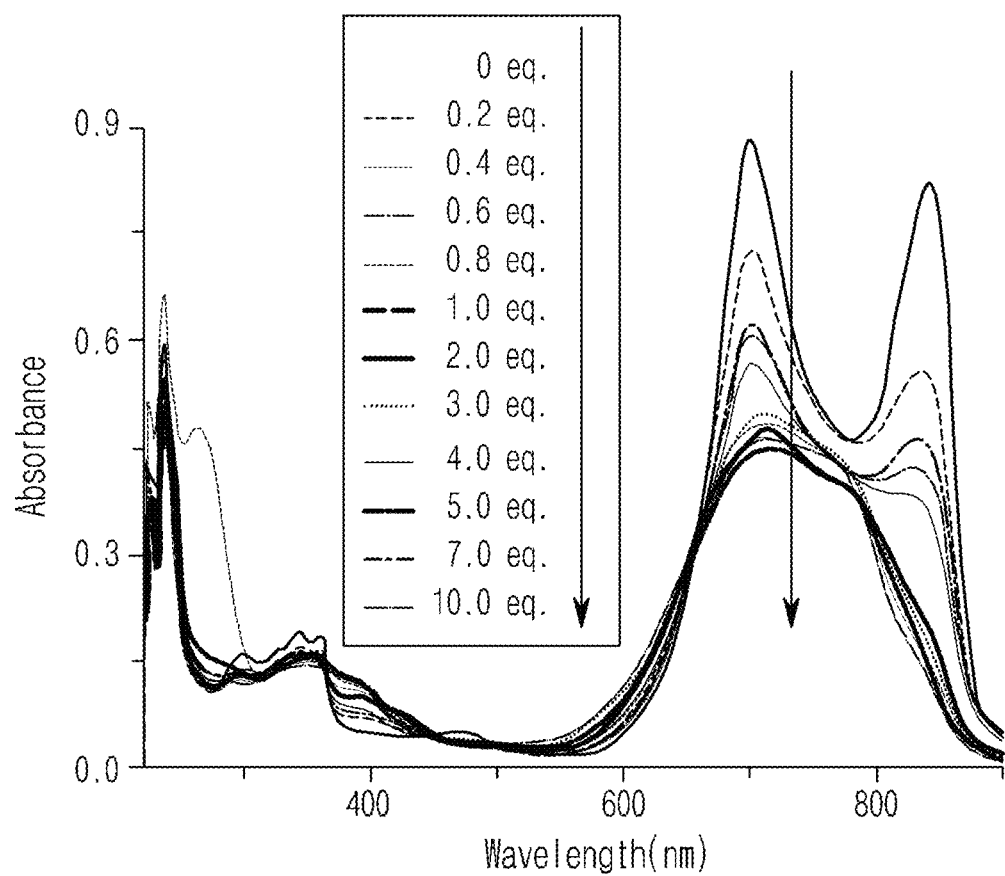

[Figure 26]
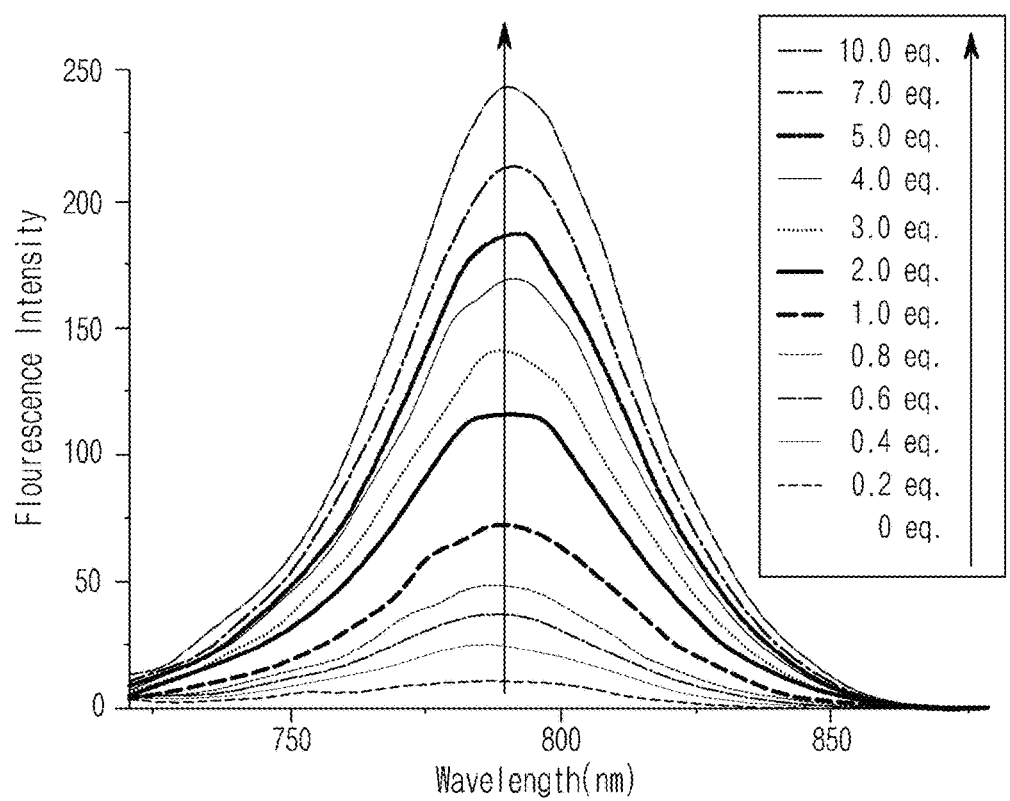

COMPOUND BASED ON CYANINE SCAFFOLD FOR DIAGNOSIS SEPSIS BY SELECTIVELY DETECT GLUTATHIONE

CROSS-REFERENCES TO RELATED APPLICATION

This patent application claims the benefit of priority from Korean Patent Application No. 10-2014-0127887, filed on Sep. 24, 2014 and Korean Patent Application No. 10-2015-0038035, filed on Mar. 19, 2015 the contents of which are incorporated herein by reference.

BACKGROUND OF THE INVENTION

1. Field of the Invention

The present invention relates to a compound based on cyanine scaffold for diagnosing sepsis by selectively detecting glutathione.

2. Description of the Related Art

The amino acids containing thiol group (R—SH) are the components forming numbers of peptides playing an important role in maintaining oxidation-reduction homeostasis with keeping balance between the reduced free thiol and oxidized disulfide (non-patent reference 1).

Non-patent reference 2 describes that the abnormal levels of the amino acids containing thiol group (R—SH) are closely related to the development of liver injury, cancer, AIDS, osteoporosis, Alzheimer's disease, inflammatory bowel disease, and cardiovascular disease, etc. That is, if we measure and judge the level of biothiol, the amino acid that contains thiol group (R—SH), we can make early diagnosis for the related diseases.

Thus, a variety of fluorescent probes have been developed to detect selectively the amino acid containing thiol group (R—SH) among various amino acids in vivo. Particularly, according to non-patent reference 3, a probe is described in relation to the unique nucleophilic addition and substitution of thiol group. However, this probe does not select a specific amino acid containing thiol group (R—SH) each and selectively but select all the biothiols that contain R—SH such as cysteine, homocysteine, and glutathione, which draws a limitation in selective detection of each target amino acid.

Among these biothiols, glutathione is involved in cell functions, for example, intracellular redox activity, xenobiotic metabolism, intracellular signaling, and gene regulation, and also plays an important role in protecting cell damage caused by free radicals and reactive oxygen species. More precisely, glutathione is reacted to oxides in vivo, resulting in reversible glutathione disulfide (GSSG) that is the oxidized form of glutathione wherein two glutathione molecules are connected each other by disulfide bond (—S—S). By this reaction, in vivo oxidation-reduction potential is regulated.

To detect the said glutathione selectively, a few fluorescent probes based on organic dyes have been developed. For example, non-patent reference 4 describes the promising probe based on bis-spiropyran structure. Non-patent reference 5 describes the probe based on resorufin structure to detect selectively glutathione in blood plasma. Non-patent reference 6 describes the fluorescent sensor based on BODIPY structure to detect selectively glutathione in living cells.

Considering glutathione is a major intracellular antioxidant that exists in cell at the concentration of approximately 0.5~10 mM, the detection of in vivo glutathione by using a near infrared ray (700~900 nm) fluorescent probe is advantageous because it causes less biological damage and makes deeper penetration in tissue in the said wave-length range. However, those probes developed to detect glutathione using near infrared ray demonstrated not as excellent selectivity.

In the course of study to develop a probe usable for the selective detection of in vivo glutathione, the present inventors confirmed that the compound based on cyanine scaffold identified by the inventors could keep its structure even in intracellular environment and selectively react to glutathione among many amino acids containing thiol group (R—SH), exemplified by cysteine, homocysteine, and glutathione, etc, and displayed glutathione specific absorption spectrum or fluorescence spectrum, so that it could be efficiently used not only for the detection of glutathione in biosamples but also for the diagnosis of sepsis that can change the level of in vivo glutathione, leading to the completion of this invention.

PRIOR ART REFERENCES

Non-Patent References

Wood, Z. A.; Schroder, E.; Robin Harris, J.; Poole, L. B. Trends Biochem. Sci. 2003, 28, 32.

Herzenberg, L. A.; De Rosa, S. C.; Dubs, J. G.; Roederer, M.; Anderson, M. T.; Ela, S. W.; Deresinski S. C.; Herzenberg, L. A. Proc. Natl. Acad. Sci. U.S.A. 1997, 94, 1967.

Yin, L.-L.; Chen, Z.-Z.; Tong, L.-L.; Xu, K.-H.; Tang, B. Chin. J. Analy. Chem. 2009, 37, 1073.

Shao, N.; Jin, J.; Wang, H.; Zheng, J.; Yang, R.; Chan, W.; Abliz, C. J. Am. Chem. Soc. 2010, 132, 725.

Guo, Y.; Yang, X.; Hakuna, L.; Barve, A.; Escobedo, J. O.; Lowry, M.; Strongin, R. M. Sensors 2012, 12, 5940.

Niu, L.-Y.; Guan, Y.-S.; Chen, Y.-Z.; Wu, L.-Z.; Tung, C.-H.; Yang, Q.-Z. J. Am. Chem. Soc. 2012, 134, 18928.

SUMMARY OF THE INVENTION

It is an object of the present invention to provide a compound based on cyanine scaffold to detect glutathione selectively.

It is another object of the present invention to provide a method for preparing the said compound.

It is also an object of the present invention to provide a chemical sensor for detecting the amino acid containing thiol group that comprises the said compound.

It is further an object of the present invention to provide a method for detecting the amino acid containing thiol group using the said chemical sensor.

It is also an object of the present invention to provide a composition for diagnosing bacterial disease that comprises the said compound.

It is also an object of the present invention to provide a method for diagnosing bacterial disease using the said composition.

To achieve the above objects, the present invention provides a compound represented by the below formula 1.

[Formula 1]

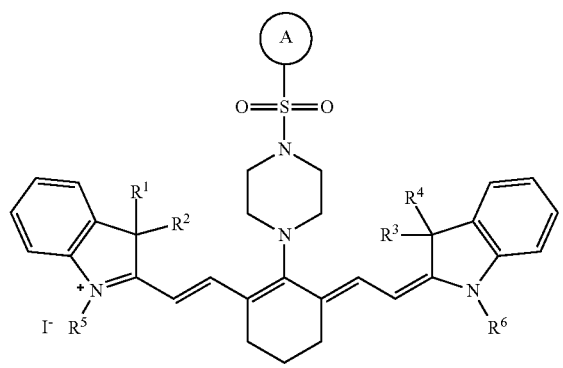

In the formula 1, $R^1, R^2, R^3, R^4, R^5$, and $R^6$ are independently —H, —OH, halogen, $C_{1-10}$ straight or branched alkyl, or $C_{1-10}$ straight or branched alkoxy;

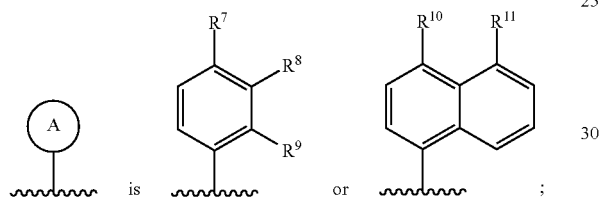

$R^7, R^8$, and $R^9$ are independently —H, —OH, —CN, —NO$_2$, halogen, $C_{1-10}$ straight or branched alkyl, or $C_{1-10}$ straight or branched alkoxy;

$R^{10}$ and $R^{11}$ are independently —H, —OH, —CN, —NO$_2$, halogen, $C_{1-10}$ straight or branched alkyl, $C_{1-10}$ straight or branched alkoxy, or —NR$^{12}$R$^{13}$, $R^{12}$ and $R^{13}$ are independently $C_{1-5}$ straight or branched alkyl;

$R^{10}$ and $R^{11}$ can be linked with neighboring carbon atoms and fused with two phenyls, and they can also form non-substituted or substituted 6-atom heterocycloalkyl containing one or more hetero atoms selected from the group consisting of N, O, and S;

And, the said substituted 6-atom heterocycloalkyl is the one wherein one or more substituents selected from the group consisting of —OH, —CN, —NO$_2$, halogen, =O, $C_{1-10}$ straight or branched alkyl, and $C_{1-10}$ straight or branched alkoxy are substituted.

The present invention also provides a method for preparing the compound represented by formula 1 comprising the following steps as shown in the below reaction formula 1:

preparing the compound represented by formula 3 by replacing the halogen of the compound represented by formula 2 with piperazine (step 1); and preparing the compound represented by formula 1 by reacting the compound represented by formula 3 prepared in step 1) with the compound represented by formula 4 (step 2).

[Reaction Formula 1]

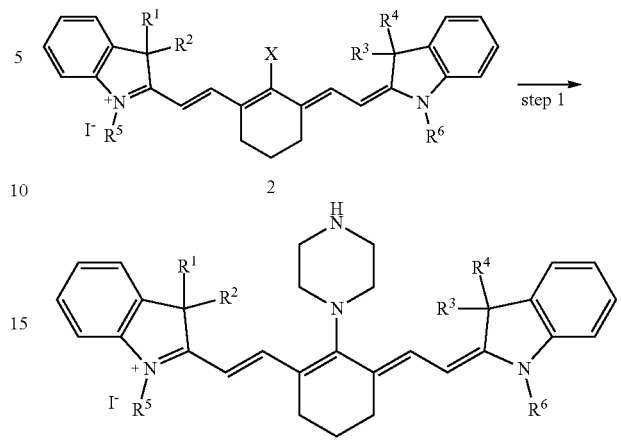

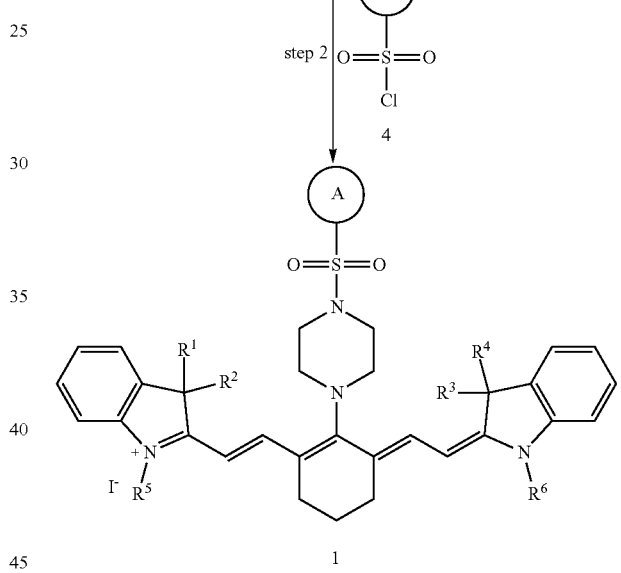

In the reaction formula 1,
X is halogen;

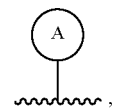

$R^1, R^2, R^3, R^4, R^5$, and $R^6$ are as defined in formula 1.

Further, the present invention provides a chemical sensor for detecting the amino acid containing thiol group comprising the compound represented by formula 1.

The present invention also provides a method for detecting the amino acid containing thiol group using the said chemical sensor.

The present invention also provides a composition for diagnosing bacterial disease comprising the compound represented by formula 1.

In addition, the present invention provides a method for diagnosing bacterial disease using the said composition.

Advantageous Effect

The compound based on cyanine scaffold of the present invention can keep its structure even in intracellular environment and can react to glutathione specifically among many amino acids containing thiol group (R—SH), exemplified by cysteine, homocysteine, and glutathione, etc, and displayed glutathione specific absorption spectrum or fluorescence spectrum, so that it can be used not only for the detection of glutathione in biosamples but also for the diagnosis of sepsis that can change the level of in vivo glutathione.

BRIEF DESCRIPTION OF THE DRAWINGS

The application of the preferred embodiments of the present invention is best understood with reference to the accompanying drawings, wherein:

FIG. 1 presents the image of absorption spectrum generated when the compound prepared in Example 1 and various in vivo amino acids were added respectively to HEPES (4-(2-hydroxyethyl)piperazine-1-ethanesulfonic acid) buffer containing 10% dimethylsulfoxide (DMSO), FIG. 2 presents the image of fluorescence spectrum generated when the compound prepared in Example 1 and various in vivo amino acids were added respectively to HEPES (4-(2-hydroxyethyl)piperazine-1-ethanesulfonic acid) buffer containing 10% dimethylsulfoxide (DMSO), FIG. 3(A) presents the fluorescence image illustrating HeLa cells observed under confocal laser scanning microscope, FIG. 3(B) presents the fluorescence image illustrating HeLa cells added with the compound prepared in Example 1, observed under confocal laser scanning microscope, FIG. 3(C) presents the fluorescence image illustrating HeLa cells pretreated with the thiol blocker, N-methylmaleimide (NMM), and added with the compound prepared in Example 1, observed under confocal laser scanning microscope, FIG. 3(D) presents the fluorescence image illustrating HeLa cells pretreated with the thiol blocker, N-methylmaleimide (NMM), and added with cysteine and the compound prepared in Example 1, observed under confocal laser scanning microscope, FIG. 3(E) presents the fluorescence image illustrating HeLa cells pretreated with the thiol blocker, N-methylmaleimide (NMM), and added with homocysteine and the compound prepared in Example 1, observed under confocal laser scanning microscope, FIG. 3(F) presents the fluorescence image illustrating HeLa cells pretreated with the thiol blocker, N-methylmaleimide (NMM), and added with glutathione and the compound prepared in Example 1, observed under confocal laser scanning microscope, FIG. 4 presents the image of fluorescence spectrum generated when the compound prepared in Example 2 and various in vivo amino acids were added respectively to HEPES (4-(2-hydroxyethyl)piperazine-1-ethanesulfonic acid) buffer containing 10% dimethylsulfoxide (DMSO), FIG. 5 presents the image illustrating the increase of fluorescence strength around 736 nm over the time after the compound prepared in Example 2 and glutathione, cysteine, and homocysteine were added to HEPES (4-(2-hydroxyethyl)piperazine-1-ethanesulfonic acid) buffer containing 10% dimethylsulfoxide (DMSO), FIG. 6 presents the image of absorption spectrum that has changed after the compound prepared in Example 2 was added to HEPES (4-(2-hydroxyethyl)piperazine-1-ethanesulfonic acid) buffer containing 10% dimethylsulfoxide (DMSO) with slowly raising the concentration of glutathione therein from 0 to 50 μM, FIG. 7 presents the image of fluorescence spectrum that has changed after the compound prepared in Example 2 was added to HEPES (4-(2-hydroxyethyl)piperazine-1-ethanesulfonic acid) buffer (10 mM, pH=7.4) containing 10% dimethylsulfoxide (DMSO) with slowly raising the concentration of glutathione therein from 0 to 50 μM, FIG. 8 presents the image of absorption spectrum that has changed over the time after the compound prepared in Example 2 and glutathione were added to HEPES (4-(2-hydroxyethyl)piperazine-1-ethanesulfonic acid) buffer containing 10% dimethylsulfoxide (DMSO), FIG. 9 presents the image of fluorescence spectrum that has changed over the time after the compound prepared in Example 2 and glutathione were added to HEPES (4-(2-hydroxyethyl)piperazine-1-ethanesulfonic acid) buffer containing 10% dimethylsulfoxide (DMSO), FIG. 10 presents the image obtained from matrix assisted laser desorption/ionization time-of-flight mass spectrometry performed after the reaction between glutathione and the compound prepared in Example 2, FIG. 11(A) presents the fluorescence image illustrating HeLa cells observed under confocal laser scanning microscope, FIG. 11(B) presents the fluorescence image illustrating HeLa cells added with the compound prepared in Example 2, observed under confocal laser scanning microscope, FIG. 11(C) presents the fluorescence image illustrating HeLa cells pretreated with the thiol blocker, N-methylmaleimide (NMM), and added with the compound prepared in Example 2, observed under confocal laser scanning microscope, FIG. 11(D) presents the fluorescence image illustrating HeLa cells pretreated with the thiol blocker, N-methylmaleimide (NMM), and added with cysteine and the compound prepared in Example 2, observed under confocal laser scanning microscope, FIG. 11(E) presents the fluorescence image illustrating HeLa cells pretreated with the thiol blocker, N-methylmaleimide (NMM), and added with homocysteine and the compound prepared in Example 2, observed under confocal laser scanning microscope, FIG. 11(F) presents the fluorescence image illustrating HeLa cells pretreated with the thiol blocker, N-methylmaleimide (NMM), and added with glutathione and the compound prepared in Example 2, observed under confocal laser scanning microscope, FIG. 14(A) presents the image of the mouse treated with nothing, obtained by in vivo imaging system (IVIS) spectrum, FIG. 14(B) presents the image of the mouse treated with N-methylmaleimide (NMM), obtained by in vivo imaging system (IVIS) spectrum, FIG. 14(C) presents the image of the mouse treated with the compound prepared in Example 2, obtained by in vivo imaging system (IVIS) spectrum, FIG. 14(D) presents the image of the mouse treated with N-methylmaleimide (NMM) and the compound prepared in Example 2, obtained by in vivo imaging system (IVIS) spectrum, FIG. 15(A) presents the image of livers of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum, FIG. 15(B) presents the image of kidneys of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum, FIG. 15(C) presents the image of lungs of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum, FIG. 15(D) presents the image of spleens of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum, FIG. 16(A) presents the image of the mouse treated with the compound prepared in Example 2, obtained by in vivo imaging system (IVIS) spectrum, FIG. 16(B) presents the image of the mouse treated with acetaminophen (APAP) and the compound prepared in Example 2 together, obtained by in vivo imaging system (IVIS) spectrum, FIG. 17(A) presents the image of livers of the mouse treated with the compound prepared in Example 2 and the mouse treated with acetaminophen (APAP) and the compound prepared in Example 2 together, obtained by in vivo imaging system (IVIS) spectrum, FIG. 17(B) presents the image of kidneys of the mouse treated with the compound prepared in Example 2 and the mouse treated with acetaminophen (APAP) and the compound prepared in Example 2 together, obtained by in vivo imaging system (IVIS) spectrum, FIG. 17(C) presents the image of lungs of the mouse treated with the compound prepared in Example 2 and the mouse treated with acetaminophen (APAP) and the compound prepared in Example 2 together, obtained by in vivo imaging system (IVIS) spectrum, FIG. 17(D) presents the image of spleens of the mouse treated with the compound prepared in Example 2 and the mouse treated with acetaminophen (APAP) and the compound prepared in Example 2 together, obtained by in vivo imaging system (IVIS) spectrum, FIG. 18 presents the image indicating the concentration of glutathione in neutrophils of peritoneal cells of the mouse induced with sepsis and of the normal mouse, obtained by FACS (Fluorescence Activated Cell Sorting), FIG. 19 presents the fluorescence image of neutrophils, which were infected with green fluorescent protein tagged *Pseudomonas aeruginosa*, of the mouse treated with the compound prepared in Example 2, obtained by confocal laser scanning microscope, FIG. 20 presents the image illustrating two fragments of the compound prepared in Example 2 that contained piperazine, FIG. 21 presents the image illustrating three-dimensional structures of the compound of Example 1, the compound of Example 2, the compound fragment 1, and the compound fragment 2, analyzed based on DFT (Density Function Theory) at the level of B3LYP/6-31G* using Gaussian 09 program. (A) possible conformation of piperazine; (B) fragment 1; (C) fragment 2; (D) compound of example 2; (E) compound of example 1, FIG. 22 presents the image illustrating the band-gap among the compound of Example 1, the compound of Example 2, and the compound fragment 2 analyzed based on DFT (Density Function Theory) at the level of B3LYP/6-31G* using Gaussian 09 program, FIG. 23 presents the image of absorption spectrum produced in HEPES (4-(2-hydroxyethyl)piperazine-1-ethanesulfonic acid) buffer containing 10% dimethylsulfoxide (DMSO) which was added respectively with the compound prepared in Example 3 and various in vivo amino acids, FIG. 24 presents the image of fluorescence spectrum produced in HEPES (4-(2-hydroxyethyl)piperazine-1-ethanesulfonic acid) buffer containing 10% dimethylsulfoxide (DMSO) which was added respectively with the compound prepared in Example 3 and various in vivo amino acids, FIG. 25 presents the image of absorption spectrum that has changed after the compound prepared in Example 3 was added to HEPES (4-(2-hydroxyethyl)piperazine-1-ethanesulfonic acid) buffer containing 10% dimethylsulfoxide (DMSO) with slowly raising the concentration of glutathione therein from 0 to 100 μM, FIG. 26 presents the image of fluorescence spectrum that has changed after the compound prepared in Example 3 was added to HEPES (4-(2-hydroxyethyl)piperazine-1-ethanesulfonic acid) buffer (10 mM, pH=7.4) containing 10% dimethylsulfoxide (DMSO) with slowly raising the concentration of glutathione therein from 0 to 100 μM,

DESCRIPTION OF THE PREFERRED EMBODIMENTS

Figure 12A:
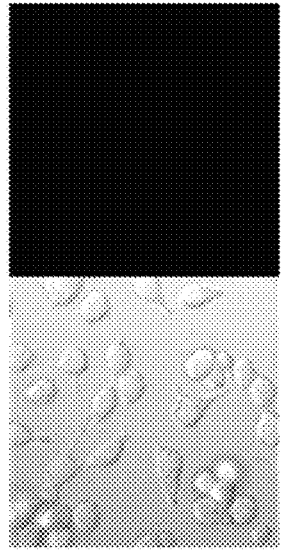
FIG. 12(A) presents the fluorescence image illustrating HeLa cells observed under confocal laser scanning microscope.

Hereinafter, the present invention is described in detail.

The present invention provides a compound represented by the below formula 1.

[Formula 1]

[Chemical structure of Formula 1 showing a symmetric compound with two indole groups connected via vinyl linkers to a central cyclohexene ring, which bears a piperazine substituted with a sulfonyl group attached to A. R1, R2 are on left indole; R3, R4 on right; R5, R6 on nitrogens; I⁻ counterion]

In the formula 1, $R^1$, $R^2$, $R^3$, $R^4$, $R^5$, and $R^6$ are independently —H, —OH, halogen, $C_{1-10}$ straight or branched alkyl, or $C_{1-10}$ straight or branched alkoxy;

[Structure definitions for A: A—is— phenyl with R7, R8, R9 substituents —or— naphthyl with R10, R11 substituents;]

$R^7$, $R^8$, and $R^9$ are independently —H, —OH, —CN, —NO$_2$, halogen, $C_{1-10}$ straight or branched alkyl, or $C_{1-10}$ straight or branched alkoxy;

$R^{10}$ and $R^{11}$ are independently —H, —OH, —CN, —NO$_2$, halogen, $C_{1-10}$ straight or branched alkyl, $C_{1-10}$ straight or branched alkoxy, or —NR$^{12}$R$^{13}$, $R^{12}$ and $R^{13}$ are independently $C_{1-5}$ straight or branched alkyl;

$R^{10}$ and $R^{11}$ can be linked with neighboring carbon atoms and fused with two phenyls, and they can also form non-substituted or substituted 6-atom heterocycloalkyl containing one or more hetero atoms selected from the group consisting of N, O, and S;

And, the said substituted 6-atom heterocycloalkyl is the one wherein one or more substituents selected from the group consisting of —OH, —CN, —NO$_2$, halogen, =O, $C_{1-10}$ straight or branched alkyl, and $C_{1-10}$ straight or branched alkoxy are substituted.

Preferably, $R^1$, $R^2$, $R^3$, $R^4$, $R^5$, and $R^6$ are independently —H, $C_{1-10}$ straight or branched alkyl, or $C_{1-10}$ straight or branched alkoxy;

[Structure definitions for A: A—is— phenyl with R7, R8, R9 substituents —or— naphthyl with R10, R11 substituents;]

$R^7$, $R^8$, and $R^9$ are independently —H, —NO$_2$, $C_{1-10}$ straight or branched alkyl, or $C_{1-10}$ straight or branched alkoxy;

$R^{10}$ and $R^{11}$ are independently —H, —NO$_2$, $C_{1-10}$ straight or branched alkyl, $C_{1-10}$ straight or branched alkoxy, or —NR$^{12}$R$^{13}$, $R^{12}$ and $R^{13}$ are independently $C_{1-5}$ straight or branched alkyl;

$R^{10}$ and $R^{11}$ can be linked with neighboring carbon atoms and fused with two phenyls, and they can also form non-substituted or substituted 6-atom heterocycloalkyl containing one or more hetero atoms selected from the group consisting of N, O, and S;

And, the said substituted 6-atom heterocycloalkyl is the one wherein one or more substituents selected from the group consisting of —NO$_2$, halogen, =O, $C_{1-10}$ straight or branched alkyl, and $C_{1-10}$ straight or branched alkoxy are substituted.

More preferably, $R^1$, $R^2$, $R^3$, $R^4$, $R^5$, and $R^6$ are independently $C_{1-10}$ straight or branched alkyl;

[Structure definitions for A: A—is— phenyl with R7, R8, R9 substituents —or— naphthyl with R10, R11 substituents;]

$R^7$, $R^8$, and $R^9$ are independently —H or —NO$_2$;

$R^{10}$ and $R^{11}$ are independently —H or —NR$^{12}$R$^{13}$, $R^{12}$ and $R^{13}$ are independently $C_{1-5}$ straight or branched alkyl;

$R^{10}$ and $R^{11}$ can be linked with neighboring carbon atoms and fused with two phenyls, and they can also form non-substituted or substituted 6-atom heterocycloalkyl containing one or more Ns;

And, the said substituted 6-atom heterocycloalkyl is the one wherein one or more substituents selected from the group consisting of =O and $C_{1-10}$ straight or branched alkyl are substituted.

The present invention also provides a method for preparing the compound represented by formula 1 comprising the following steps as shown in the below reaction formula 1:

preparing the compound represented by formula 3 by replacing the halogen (X) of the compound represented by formula 2 with piperazine (step 1); and preparing the compound represented by formula 1 by reacting the compound represented by formula 3 prepared in step 1) with the compound represented by formula 4 (step 2).

[Reaction Formula 1]

[Structure of compound 2: symmetric bis-indolyl compound with central cyclohexene bearing X (halogen) substituent, R1, R2, R3, R4 on indole rings, R5, R6 on nitrogens, I⁻ counterion] →step 1

2

-continued

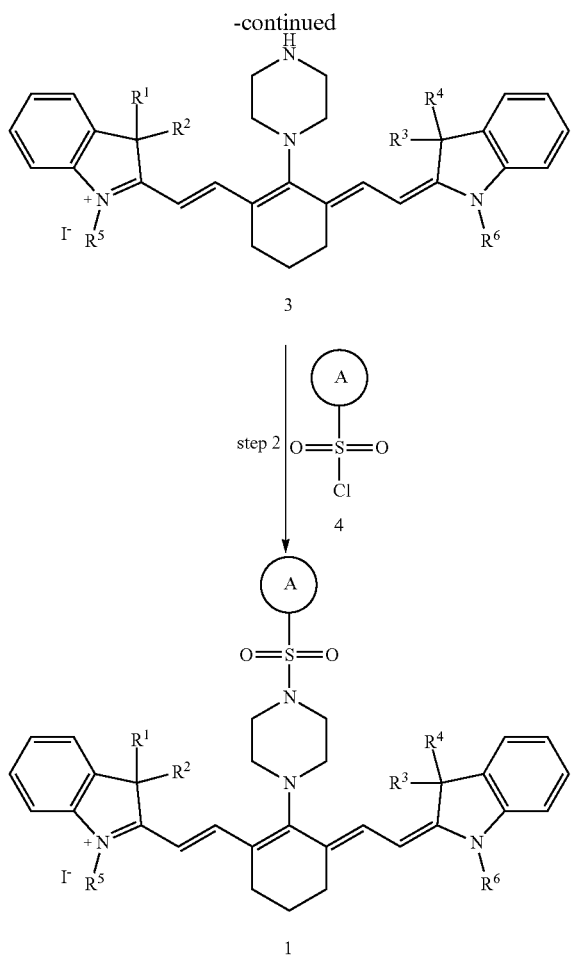

3

In the reaction formula 1,
X is halogen;

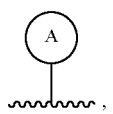, $R^1$, $R^2$, $R^3$, $R^4$, $R^5$, and $R^6$ are as defined in formula 1.

The method for preparing the compound represented by formula 1 of the invention is described in more detail hereinafter.

In the method for preparing the compound represented by formula 1 according to the present invention, step 1) is to prepare the compound represented by formula 3 by replacing the halogen (X) of the compound represented by formula 2 with piperazine. More precisely, the compound represented by formula 2 was dissolved in a solvent, to which piperazine was added, followed by stirring. Column chromatography was performed, through which the purified compound represented by formula 3 was prepared.

At this time, the solvent was preferably selected from the group consisting of tetrahydrofuran; dioxane; ether solvents including ethylether and 1,2-dimethoxyethane; lower alcohols including methanol, ethanol, propanol and butanol; dimethylformamide (DMF), dimethylsulfoxide (DMSO), dichloromethane (DCM), dichloroethane, water, acetonigensulfonate, toluenesulfonate, chlorobenzenesulfonate, xylensulfonate, phenylacetate, phenylpropionate, phenylbutylate, citrate, lactate, β-hydroxybutylate, glycolate, malate, tartlate, methanesulfonate, propanesulfonate, naphthalene-1-sulfonate, naphthalene-2-sulfonate, and mandelate, and dimethylformamide was more preferred as the solvent.

The reaction temperature was preferably set in the range of 0° C.~boiling point of the selected solvent, and the reaction time was not limited, but 0.5~10 hours were preferred.

In the method for preparing the compound represented by formula 1 according to the present invention, step 2) is to prepare the compound represented by formula 1 by reacting the compound represented by formula 3 prepared in step 1) with the compound represented by formula 4. More precisely, a base was added to the compound represented by formula that was dissolved in a solvent, followed by stirring. The compound represented by formula 4 which was dissolved in a solvent was added to the above drop by drop, followed by stirring. Silica gel chromatography was performed to obtain the purified compound represented by formula 3.

At this time, the solvent was preferably selected from the group consisting of tetrahydrofuran; dioxane; ether solvents including ethylether and 1,2-dimethoxyethane; lower alcohols including methanol, ethanol, propanol and butanol; dimethylformamide (DMF), dimethylsulfoxide (DMSO), dichloromethane (DCM), dichloroethane, water, acetonigensulfonate, toluenesulfonate, chlorobenzenesulfonate, xylensulfonate, phenylacetate, phenylpropionate, phenylbutylate, citrate, lactate, β-hydroxybutylate, glycolate, malate, tartlate, methanesulfonate, prpanesulfonate, naphthalene-1-sulfonate, naphthalene-2-sulfonate, and mandelate, and dichloromethane was more preferred as the solvent.

The base herein was preferably selected from the group consisting of triethylamine (TEA), potassium hydroxide (KOH), sodium hydroxide (NaOH), lithium hydroxide (LiOH), and cesium carbonate ($Cs_2CO_3$), and triethylamine (TEA) was more preferred as the base.

The reaction temperature was preferably set in the range of 0° C.~boiling point of the selected solvent, and the reaction time was not limited, but 0.5~10 hours were preferred.

The present invention also provides a chemical sensor for detecting the amino acid containing thiol group that comprises the compound represented by formula 1. Herein, the amino acid containing thiol group is selected from the group consisting of cysteine, homocysteine, and glutathione, and particularly glutathione is preferred.

The present invention also provides a method for detecting the amino acid containing thiol group using the said chemical sensor. Herein, the amino acid containing thiol group is preferably selected from the group consisting of cysteine, homocysteine, and glutathione, and particularly glutathione is more preferred.

The mechanism of the detection above is as follows: When the compound represented by formula 1 reacts to glutathione, the sulfonyl-phenyl derivative substituted in the compound represented by formula 1 is fallen apart, resulting in the cyanine derivative compound having free piperazine. Among the sulfonyl-phenyl derivatives fallen apart therefrom, the phenyl derivative is conjugated with thiol group in glutathione, during which absorption or fluorescence is changed. So, the changes of absorption or fluorescence alone or together can be screened, leading to the detection of the amino acid containing thiol group.

The present invention also provides a composition for diagnosing bacterial disease comprising the compound represented by formula 1. Herein, the bacterial disease is sepsis.

In addition, the present invention provides a method for diagnosing bacterial disease using the said composition. Herein, the bacterial disease is sepsis.

In general, once caught sepsis, neutrophils, a kind of leucocytes, produce excessive amount of ROS (Reactive Oxygen Species) because of oxidative stress. This excessive ROS causes disorders in neuron, skin, and digestive system, etc. Glutathione that is an antioxidant capable of regulating oxidation/reduction potential reacts to the excessive ROS generated by sepsis, so that it can be converted to reversible glutathione disulfide (GSSG), that is an oxidized glutathione. Thus, the in vivo glutathione is down-regulated accordingly, by which sepsis can be diagnosed.

To investigate the changes of absorption or fluorescence, which is the principle of glutathione detection for the chemical sensor, and the usability thereof for the diagnosis of sepsis, the following experiments were performed.

First, the following experiment was performed to investigate the usability of the compound prepared in Example 1 for the detection of cysteine, homocysteine, and glutathione, among many biothiols which are the amino acids containing thiol group (R—SH). As a result, the compound prepared in Example 1 reacted to such amino acids containing thiol group (R—SH) as cysteine, homocysteine, and glutathione in biosamples, to cause changes in absorption and fluorescence spectrum (see FIGS. 1 and 2 of Experimental Example 1).

In the meantime, the following experiment was also performed to investigate the usability of the compound prepared in Example 1 for the detection of intracellular biothiols which are the amino acids containing thiol group (R—SH), for example for the detection of cysteine, homocysteine, and glutathione. As a result, when it was introduced in HeLa cells, the compound prepared in Example 1 reacted to such amino acids containing thiol group (R—SH) as cysteine, homocysteine, and glutathione, which exist in cytoplasm, so that a strong red fluorescence was observed under confocal laser scanning microscope (see FIG. 3 of Experimental Example 2).

To evaluate the glutathione selectivity of the compound prepared in Example 2, the following experiment was performed. As a result, the compound prepared in Example 2 selectively reacted to glutathione alone among many amino acids containing thiol group (R—SH) such as cysteine, homocysteine, and glutathione, with showing glutathione specific fluorescence spectrum (see FIGS. 4 and 5 of Experimental Example 3).

To investigate the changes of absorption or fluorescence spectrum of the compound prepared in Example 2 according to the concentration of glutathione (GSH), the following experiment was performed. As a result, the reaction of the compound prepared in Example 2 depended on the concentration of glutathione (see FIGS. 6 and 7 of Experimental Example 4).

Further, the reaction between glutathione (GSH) and the compound prepared in Example 2 was induced. And then the changes of absorption or fluorescence spectrum over the time were investigated by the following experiment. As a result, the compound prepared in Example 2 reacted to glutathione to change absorption or fluorescence spectrum fast (see FIGS. 8 and 9 of Experimental Example 5).

To understand the reaction mechanism between glutathione and the compound prepared in Example 2, matrix assisted laser desorption/ionization time-off-flight mass spectrometry was performed, in which glutathione and the compound prepared in Example 2 were reacted. As a result, the changes of absorption or fluorescence spectrum according to the reaction between glutathione and the compound based on cyanine scaffold of the present invention were confirmed to be attributed to the reaction presented in FIG. 10 (see FIG. 10 of Experimental Example 6).

To evaluate the selection specificity of the compound prepared in Example 2 to cysteine, homocysteine, and glutathione, among many biothiols that are the intracellular amino acids containing thiol group (R—SH), the following experiment was performed. As a result, when the compound prepared in Example 2 was introduced in HeLa cells, it selectively reacted to glutathione alone among many intracellular amino acids containing thiol group (R—SH) such as cysteine, homocysteine, and glutathione, by which a strong red fluorescence was observed under confocal laser scanning microscope (see FIG. 11 of Experimental Example 7).

It was further investigated whether glutathione could be down-or up-regulated by an oxidant. To do so, HeLa cells containing the antioxidant glutathione that had been prepared in Experimental Example 2 were treated with 100 μM of $H_2O_2$, the oxidant, at 37° C. for minutes to induce the changes of glutathione concentration. 20 μM of the compound prepared in Example 2 was also added thereto, followed by culture at 37° C. for 20 minutes. The cells were washed with DPBS (Dulbecco's Phosphate Buffered Saline) three times to eliminate the remaining compound, followed by imaging with confocal laser scanning microscope (Fluoview 1200, Olympus, Japan). At this time, the emitting filter with the excitation wavelength of 653 nm and the band-path (BP) of 655~755 nm was used. The concentration of the intracellular glutathione could be measured by the strength of the red fluorescence emitted from the compound prepared in Example 2. Also, since the compound prepared in Example 2 did not reacted to the oxidized glutathione disulfide (GSSG), it could be concluded that the compound had excellent selectivity to glutathione (see FIG. 12 of Experimental Example 8).

To observe the changes of glutathione level in the presence of an oxidant, RAW 264.7 cells (macrophage cell line, Korea Cell Line Bank) were cultured in RPMI 1640 (Roswell Park Memorial Institute) supplemented with 10% heat-inactivated fetal bovine serum (FBS), 100 U/mL penicillin, and 100 U/mL streptomycin in a 37° C. 5% $CO_2$ incubator. The RAW 264.7 cells were treated with lipopolysaccharide (LPS) for 20 minutes at the concentration of 1 μg/mL, and with interferon-γ for 16 hours at the concentration of 50 ng/mL, and with phorbol 12-myristate 13-acetate (PMA) for 20 minutes at the concentration of 20 μM to induce the generation of endogenous feroxynitrite having the characteristics of an oxidant. Then, the cells were seeded in 35-mm glass bottomed dishes at the density of $3 \times 10^5$ cells/dish in 1640 medium. 24 hours later, the compound prepared in Example 2 was treated thereto at the concentration of 20 μM for 20 minutes. The cells were washed with DPBS (Dulbecco's Phosphate Buffered Saline) three times, followed by imaging with confocal laser scanning microscope (Fluoview 1200, Olympus, Japan). At this time, the emitting filter with the excitation wavelength of 635 nm and the band-path (BP) of 655~755 nm was used. The concentration of the intracellular glutathione could be measured by the strength of the red fluorescence emitted from the compound prepared in Example 2. Also, since the compound prepared in Example 2 did not reacted to the oxidized glutathione disulfide (GSSG), it could be concluded that the compound had excellent selectivity to glutathione (see FIG. 13 of Experimental Example 9).

To evaluate whether or not the compound prepared in Example 2 could be used for the detection of in vivo glutathione in the mouse model, the following experiment was performed. As a result, the compound prepared in Example 2 was confirmed to be efficiently used for the observation of the in vivo distribution of glutathione with detecting the strength of red fluorescence on In Vivo Imaging System (IVIS) spectrum (see FIGS. 14 and 15 of Experimental Example 10, and FIGS. 16 and 17 of Experimental Example 11).

The following experiment was also performed to investigate whether or not the compound prepared in Example 2 could be used for the diagnosis of sepsis. As a result, it was confirmed that the compound prepared in Example 2 could be efficiently used for the diagnosis of sepsis by measuring the concentration of glutathione (see FIG. 18 of Experimental Example 12, and FIG. 19 of Experimental Example 13).

Further, the following experiment was performed to analyze the cause of the selectivity of the compound prepared in Example 2. As a result, the selectivity of the compound prepared in Example 2 was attributed to the shape of piperazine in the active site where the reaction between the compound and glutathione happened, the shape of dansyl group that was binding to piperazine, S—N binding length, and Band-gap energy (see FIGS. 20, 21 and 22 of Experimental Example 14).

The following experiment was performed to evaluate the glutathione (GSH) specific selectivity of the compound prepared in Example 3. As a result, the compound prepared in Example 3 reacted to glutathione alone, among many endogenous amino acids in biosamples, with displaying the changes of absorption or fluorescence spectrum, so that the compound was confirmed to be efficiently used for the detection of glutathione in biosamples (see FIGS. 23 and 24 of Experimental Example 15).

Further, the following experiment was performed to investigate whether or not the absorption or fluorescence spectrum produced by the compound prepared in Example 3 could be affected by the concentration of glutathione. As a result, the compound prepared in Example 3 reacted only with glutathione dose-dependently (see FIGS. 25 and 26 of Experimental Example 16).

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: Preparation of 2-[2-[2-chloro-3-[(1,3-dihydro-3,3-dimethyl-1-propyl-2H-indole-2-ylidene)ethylidene]-1-cyclohexene-1-yl]ethenyl]-3,3-dimethyl-1-propylindolium iodide (IR-780 iodide)

IR-780 iodide was purchased from Sigma-Aldrich Co.

Example 1: Preparation of 2-((E)-2-((E)-3-((E)-2-(3,3-dimethyl-1-propylindolium-2-ylidene)ethylidene)-2-(4-(2,4-dinitrophenylsulfonyl)piperazine-1-yl)cyclohex-1-enyl)binyl)-3,3-dimethyl-1-propyl-3H-indolium iodide Step 1: Preparation of 2-((E)-2-((E)-3-((E)-2-(3,3-dimethyl-1-propylindolin-2-ylidene)ethylidene)-2-(piperazine-1-yl)cyclohex-1-enyl)binyl)-3,3-dimethyl-1-propyl-3H-indolium iodide

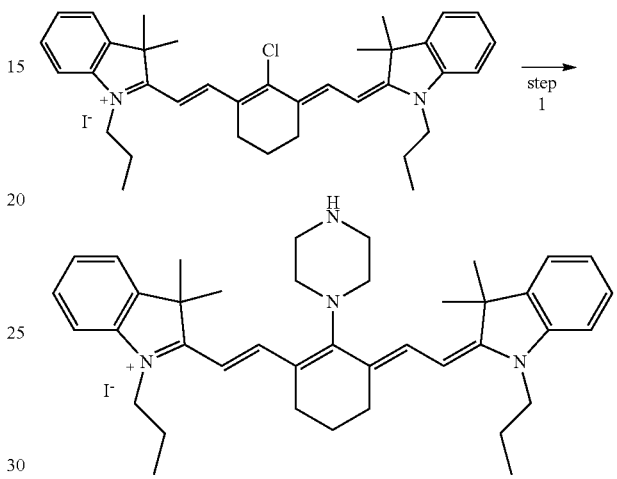

69 mg of piperazine was added to the compound prepared in Preparative Example 1 dissolved in 10 mL of anhydrous DMF (dimethylformamide) in argon environment. The reaction mixture was stirred at 85° C. for 4 hours, followed by cooling at room temperature. The solvent was eliminated under reduced pressure. The mixture was purified by silica gel chromatography using dichloromethane:methanol (40:1) as a moving phase. As a result, 136 mg of the target compound was obtained as a blue solid (yield: 85%).

$^1$H NMR (300 MHz, CDCl$_3$) δ 7.66 (d, J=15.0 Hz, 2H), 7.26-7.32 (m, 4H), 7.09 (t, J=6.0 Hz, 2H), 6.97 (d, J=6.0 Hz, 2H), 5.80 (d, J=15.0 Hz, 2H), 3.88 (m, 8H), 3.26 (t, J=6.0 Hz, 4H), 2.44 (t, J=6.0 Hz, 4H), 1.84 (m, 6H), 1.68 (s, 12H), 1.02 (t, J=6.0 Hz, 6H).
$^{13}$C NMR (75 MHz, CDCl$_3$) δ 173.3, 169.1, 142.8, 141.0, 140.3, 128.3, 123.7, 123.5, 122.2, 109.4, 85.9, 55.3, 48.2, 47.2, 45.2, 29.2, 25.0, 21.8, 20.3, 11.8. ESI MS m/z=589.6 [M–I$^-$]$^+$; calcd exact mass 716.3.

Step 2: Preparation of 2-((E)-2-((E)-3-((E)-2-(3,3-dimethyl-1-propylindolin-2-ylidene)ethylidene)-2-(4-(2,4-dinitrophenylsulfonyl)piperazine-1-yl)cyclohex-1-enyl)binyl)-3,3-dimethyl-1-propyl-3H-indolium iodide

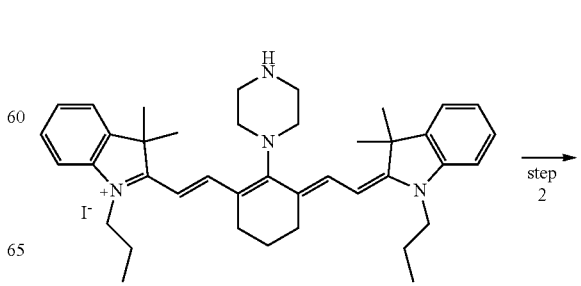

-continued

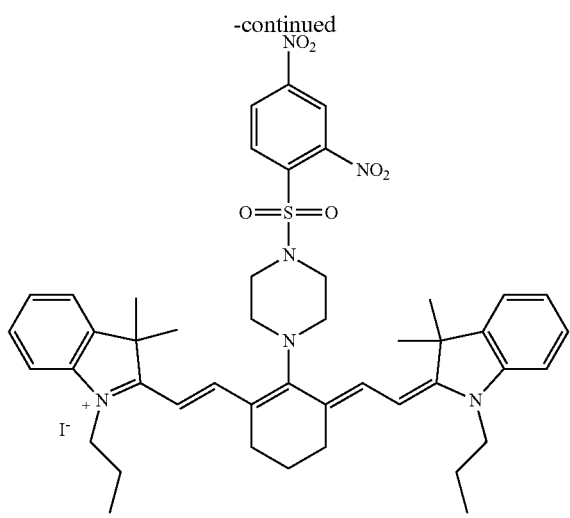

30 mg of Et$_3$N was added to the compound prepared in step 1) dissolved in 10 mL of anhydrous dichloromethane in argon environment. After stirring the reaction mixture for 5 minutes, 53 mg of 2,4-dinitrobenzene-1-sulfonyl chloride dissolved in 5 mL of dichloromethane was added to the mixture drop by drop at 0° C. After stirring the mixture at room temperature for 4 hours, the solvent was eliminated from the mixture under reduced pressure. The mixture was purified by silica gel chromatography using dichloromethane:methanol (30:1) as a moving phase. As a result, 167 mg of the target compound was obtained as a blue solid (yield: 75%).

$^1$H NMR (300 MHz, CDCl$_3$) δ 8.77 (m, 2H), 8.52 (s, 1H), 7.80 (d, J=15.0 Hz, 2H), 7.35 (m, 4H), 7.21 (m, 2H), 7.06 (d, J=9.0 Hz, 2H), 5.95 (d, J=15.0 Hz, 2H), 3.96 (t, J=6.0 Hz, 4H), 3.76 (d, J=6.0 Hz, 4H), 3.69 (d, J=6.0 Hz, 4H), 2.49 (t, J=6.0 Hz, 4H), 1.86 (m, 6H), 1.66 (s, 12H), 1.05 (t, J=6.0 Hz, 6H).

$^{13}$C NMR (75 MHz, CDCl$_3$) δ 170.4, 169.9, 149.8, 147.9, 142.5, 141.9, 140.5, 136.8, 134.9, 128.6, 127.8, 126.3, 124.5, 122.2, 119.4, 110.0, 98.2, 54.0, 48.6, 47.8, 45.6, 28.9, 25.3, 21.5, 20.6, 11.7. MALDI-TOF MS m/z=820.5 [M−I$^−$]$^+$; calcd exact mass 946.3.

Example 2: Preparation of 2-((E)-2-((E)-3-((E)-2-(3,3-dimethyl-1-propylindolin-2-ylidene)ethylidene)-2-(4-(5-(dimethylamino)naphthalene-1-ylsulfonyl)piperazine-1-yl)cyclohex-1-enyl)binyl)-3,3-dimethyl-1-propyl-3H-indolium iodide Step 1: Preparation of 2-((E)-2-((E)-3-((E)-2-(3,3-dimethyl-1-propylindolin-2-ylidene)ethylidene)-2-(piperazine-1-yl)cyclohex-1-enyl)binyl)-3,3-dimethyl-1-propyl-3H-indolium iodide

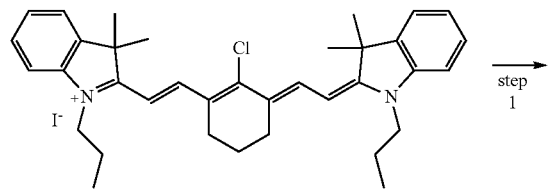

-continued

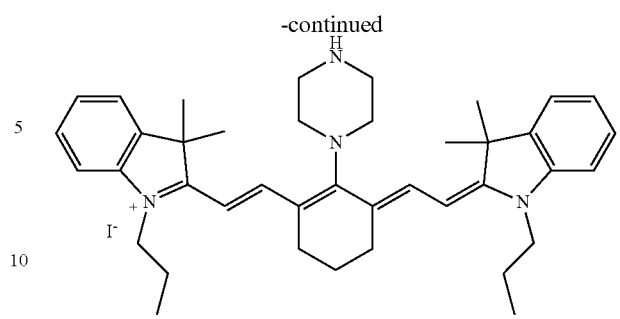

The target compound was obtained by the same manner as described in step 1) of Example 1.

Step 2: Preparation of 2-((E)-2-((E)-3-((E)-2-(3,3-dimethyl-1-propylindolin-2-ylidene)ethylidene)-2-(4-(5-(dimethylamino)naphthalene-1-ylsulfonyl)piperazine-1-yl)cyclohex-1-enyl)binyl)-3,3-dimethyl-1-propyl-3H-indolium iodide

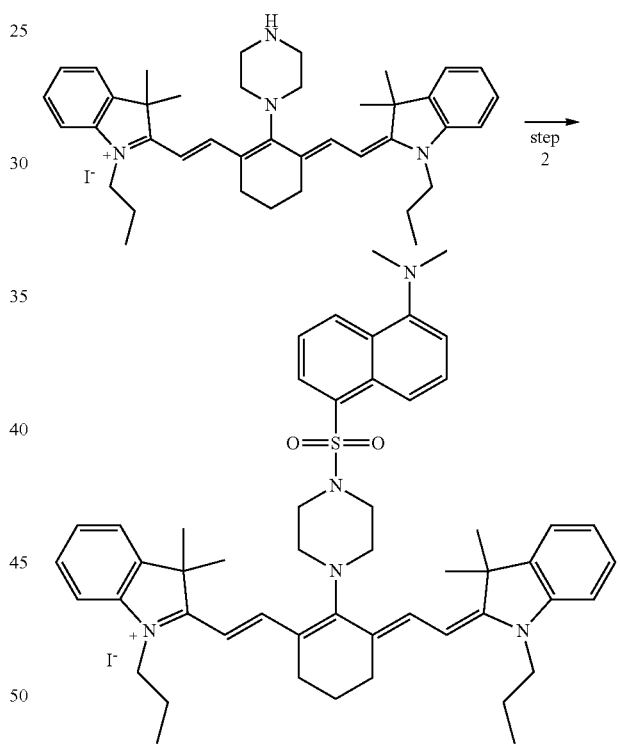

30 mg of Et$_3$N was added to the compound prepared in step 1) dissolved in 10 mL of anhydrous dichloromethane in argon environment. After stirring the reaction mixture for 5 minutes, 53 mg of 5-(dimethylamino)naphthalene-1-sulfonyl chloride dissolved in 5 mL of dichloromethane was added to the mixture drop by drop at 0° C. After stirring the mixture at room temperature for 4 hours, the solvent was eliminated from the mixture under reduced pressure. The mixture was purified by silica gel chromatography using dichloromethane:methanol (30:1) as a moving phase. As a result, 167 mg of the target compound was obtained as a blue solid (yield: 82%).

$^1$H NMR (300 MHz, CDCl$_3$) δ 8.76 (d, J=9.0 Hz, 1H), 8.60 (d, J=9.0 Hz, 1H), 8.32 (d, J=9.0 Hz, 1H), 7.59-7.70 (m,

5H), 7.36 (m, 2H), 7.18-7.28 (m, 4H), 7.08 (d, J=9.0 Hz, 2H), 5.95 (d, J=15.0 Hz, 2H), 3.99 (t, J=6.0 Hz, 4H), 3.55 (d, J=6.0 Hz, 4H), 3.41 (d, J=6.0 Hz, 4H), 2.96 (s, 6H), 2.47 (t, J=6.0 Hz, 4H), 1.83 (m, 6H), 1.29 (s, 12H), 1.02 (t, J=6.0 Hz, 6H).

$^{13}$C NMR (75 MHz, CDCl$_3$) δ 170.4, 168.9, 152.0, 142.5, 141.7, 140.5, 132.0, 130.9, 130.1, 128.7, 128.6, 127.2, 124.4, 123.6, 122.0, 110.3, 98.8, 53.3, 48.3, 47.6, 45.8, 45.6, 28.2, 25.4, 21.5, 20.6, 11.7. MALDI-TOF MS m/z=822.7 [M−I$^-$]$^+$; calcd exact mass 949.4.

Example 3: Preparation of 2-((E)-2-((E)-2-(4-((2-butyl-1,3-dioxo-2,3-dihydro-1H-benzeneisoquinoline-6-yl)sulfonyl)piperazine-1-yl)-3-((E)-2-(3,3-dimethyl-1-propylindolin-2-ylidene)ethylidene)cyclohex-1-en-1-yl)binyl)-3,3-dimethyl-1-propyl-3H-indolium iodide Step 1: Preparation of 2-((E)-2-((E)-3-((E)-2-(3,3-dimethyl-1-propylindolin-2-ylidene)ethylidene)-2-(piperazine-1-yl)cyclohex-1-enyl)binyl)-3,3-dimethyl-1-propyl-3H-indolium iodide

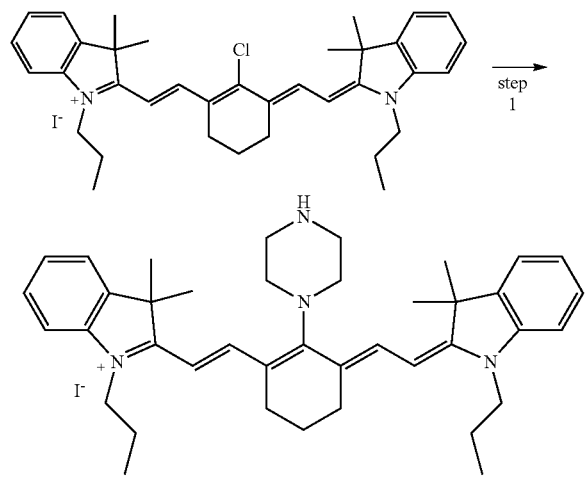

The target compound was obtained by the same manner as described in step 1) of Example 1.

Step 2: Preparation of 2-((E)-2-((E)-2-(4-((2-butyl-1,3-dioxo-2,3-dihydro-1H-benzeneisoquinoline-6-yl)sulfonyl)piperazine-1-yl)-3-((E)-2-(3,3-dimethyl-1-propylindolin-2-ylidene)ethylidene)cyclohex-1-en-1-yl)binyl)-3,3-dimethyl-1-propyl-3H-indolium iodide

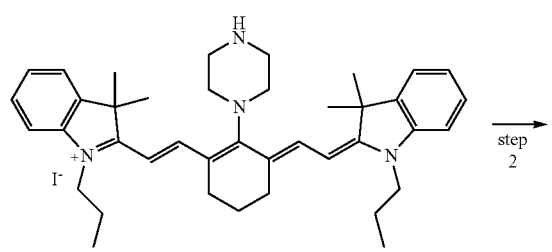

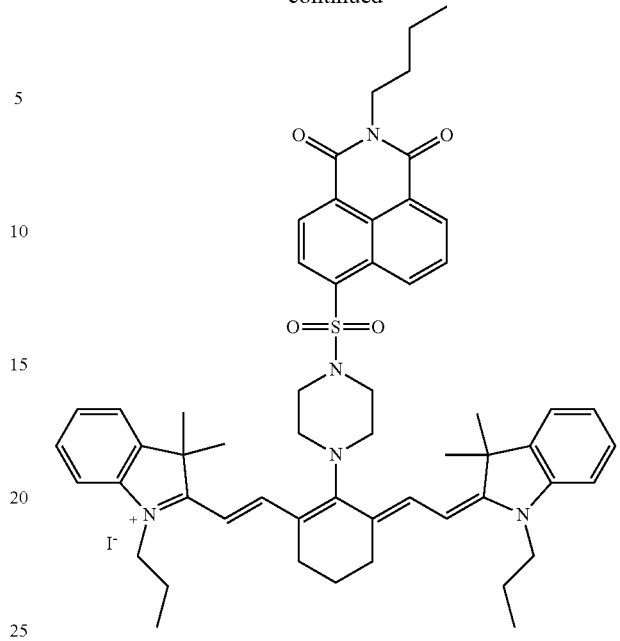

30 mg of Et$_3$N was added to the compound prepared in step 1) dissolved in 10 mL of anhydrous dichloromethane in argon environment. After stirring the reaction mixture for 5 minutes, 53 mg of 2-butyl-1,3-dioxo-2,3-dihydro-1H-benzoisoquinoline-6-sulfonyl chloride dissolved in 5 mL of dichloromethane was added to the mixture drop by drop at 0° C. After stirring the mixture at room temperature for 4 hours, the solvent was eliminated from the mixture under reduced pressure. The mixture was purified by silica gel chromatography using dichloromethane:methanol (30:1) as a moving phase. As a result, 41.5 mg of the target compound was obtained as a blue solid (yield: 27%).

$^1$H NMR (400 MHz, CDCl$_3$) δ (ppm): 9.30 (d, J=8 Hz, 1H, Ar—H), 8.82 (t, J=8 Hz, 2H, Ar—H), 8.55 (d, J=8 Hz, 1H, Ar—H), 8.12 (t, J=8 Hz, 1H, Ar—H), 7.63 (t, J=12 Hz, 2H, Ar—H), 7.37-7.34 (m, 2H, Ar—H), 7.21 (d, J=4 Hz, 4H, Ar—H), 7.07 (d, J=8 Hz, 2H, CH$_2$=CH$_2$), 5.95 (d, J=16 Hz, 2H, CH$_2$=CH$_2$), 4.25 (t, J=8 Hz, 2H, CH$_2$), 4.0 (t, J=8 Hz, 4H, CH$_2$), 3.60 (t, J=8 Hz, 4H, CH$_2$), 3.46 (t, J=8 Hz, 4H, CH$_2$), 2.49 (t, J=8 Hz, 4H, CH$_2$), 1.85-1.80 (m, 6H, CH$_2$), 1.75 (t, J=8 Hz, 2H, CH$_2$), 1.47 (t, J=8 Hz, 2H, CH$_2$), 1.36 (s, 12H, CH$_3$), 1.04 (t, J=8 Hz, 6H, CH$_3$), 0.97 (t, J=8 Hz, 3H, CH$_3$).

$^{13}$C NMR (75 MHz, CDCl$_3$) (100 MHz, CDCl$_3$): δ (ppm): 170.42, 169.03, 163.50, 162.92, 142.70, 141.79, 140.52, 129.87, 129.33, 128.89, 127.50, 127.40, 12 4.74, 122.11, 110.49, 99.12, 53.53, 48.51, 47.79, 46.03, 40.88, 30.36, 28.70, 25.64, 20.81, 20.54, 11.92. ESIm/z=1031.78. [M]; calculated exact mass=1031.39. ESI m/z=1031.78 [M]; calculated exact mass=1031.39.

Chemical structures of the compounds prepared in Example 1~Example 3 are presented in Table 1.

TABLE 1

| Example | Chemical Structure |
|---------|-------------------|
| 1 | (structure with NO₂ groups, sulfonyl, piperazine, bis-indolium cyanine with I⁻ counterion) |
| 2 | (structure with dimethylamino-naphthalene, sulfonyl, piperazine, bis-indolium cyanine with I⁻ counterion) |
| 3 | (structure with naphthalimide N-butyl, sulfonyl, piperazine, bis-indolium cyanine with I⁻ counterion) |

Experimental Example 1: Evaluation of the Detection of Biothiol

The following experiment was performed to investigate the capability of the compound prepared in Example 1 of detecting cysteine, homocysteine, and glutathione, among many biothiols which are the amino acids containing thiol group (R—SH).

<1-1> Observation of Absorption Spectrum

10 μM of the compound prepared in Example 1 and 100 μM of each endogenous amino acid (glutathione, cysteine, homocysteine, dithiothreitol, phenylalanine, histidine, glutamine, lysine, glutamate, glycine, serine, alanine, arginine, methionine, tyrosine) were added to HEPES (4-(2-hydroxyethyl)piperazine-1-ethanesulfonic acid) buffer (10 mM, pH=7.4) containing 10% dimethylsulfoxide (DMSO), followed by observation of absorption spectrum presented through UV-vis sepctra (Scinco 3000 spectrophotometer, 1 cm quartz cell) at 25° C. The results are shown in FIG. 1.

FIG. 1 presents the image of absorption spectrum generated when the compound prepared in Example 1 and various in vivo amino acids were added respectively to HEPES (4-(2-hydroxyethyl)piperazine-1-ethanesulfonic acid) buffer containing 10% dimethylsulfoxide (DMSO).

As shown in FIG. 1, the amino acids containing thiol group (R—SH) (glutathione, cysteine, homocysteine, dithiothreitol, etc) displayed a strong absorption strength at 750 nm, while the other amino acids not-containing thiol group (R—SH) displayed a weak absorption strength at 750 nm.

<1-2> Observation of Fluorescence Spectrum

The following experiment was performed by the same manner as described in Experimental Example <1-1> except that fluorescence spectrum was observed by using RF-5310/PC fluorescence spectrometer (Shimada, 1 cm quartz cell) instead of observing absorption spectrum via UV-vis sepctra (Scinco 3000 spectrophotometer, 1 cm quartz cell) ($\lambda_{ex}$=730 nm, $\lambda_{em}$=736 nm, slit:10/10 nm). The results are shown in FIG. 2.

FIG. 2 presents the image of fluorescence spectrum generated when the compound prepared in Example 1 and various in vivo amino acids were added respectively to HEPES (4-(2-hydroxyethyl)piperazine-1-ethanesulfonic acid) buffer containing 10% dimethylsulfoxide (DMSO).

As shown in FIG. 2, the amino acids containing thiol group (R—SH) (glutathione, cysteine, homocysteine, dithiothreitol, etc) displayed a strong fluorescence strength at 736 nm, while the other amino acids not-containing thiol group (R—SH) displayed a weak fluorescence strength at 736 nm.

Therefore, it was confirmed that the compound prepared in Example 1 reacted to such amino acids containing thiol group (R—SH) as cysteine, homocysteine, and glutathione in biosamples, to cause changes in absorption and fluorescence spectrum, so that it can be efficiently used for the detection of such amino acids containing thiol group (R—SH) in biosamples.

Experimental Example 2: Evaluation of the Detection of Intracellular Biothiol 1

The following experiment was performed to evaluate the selective detection capacity of the compound prepared in Example 1 for cysteine, homocysteine, and glutathione, among many biothiols that are the amino acids containing thiol group (R—SH).

HeLa cells (human adenocarcinoma cells, Korea Cell Line Bank) were cultured in RPMI 1640 (Roswell Park Memorial Institute) supplemented with 10% heat-inactivated fetal bovine serum (FBS), 100 U/mL penicillin, and 100 U/mL streptomycin in a 37° C. 5% $CO_2$ incubator. The cells were either treated or not treated with 1 mM of N-methylmaleimide (NMM) known as a thiol blocker for 20 minutes. 100 μM of each amino acid containing thiol group (R—SH) such as cysteine, homocysteine, and glutathione was added thereto. Then, the cells were seeded in 35-mm glass bottomed dishes at the density of 3×10$^5$ cells/dish in 1640 medium. 24 hours later, 10 μM of the compound prepared in Example 1 was added thereto, followed by culture at 37° C. for 20 minutes. The cells were washed with DPBS (Dulbecco's Phosphate Buffered Saline) twice to eliminate the remaining compound, followed by imaging with confocal laser scanning microscope (Fluoview 1200, Olympus, Japan). At this time, the emitting filter with the excitation wavelength of 635 nm and the band-path (BP) of 655~755 nm was used. The results are shown in FIG. 3.

FIG. 3(A) presents the fluorescence image illustrating HeLa cells observed under confocal laser scanning microscope, FIG. 3(B) presents the fluorescence image illustrating HeLa cells added with the compound prepared in Example 1, observed under confocal laser scanning microscope, FIG. 3(C) presents the fluorescence image illustrating HeLa cells pretreated with the thiol blocker, N-methylmaleimide (NMM), and added with the compound prepared in Example 1, observed under confocal laser scanning microscope, FIG. 3(D) presents the fluorescence image illustrating HeLa cells pretreated with the thiol blocker, N-methylmaleimide (NMM), and added with cysteine and the compound prepared in Example 1, observed under confocal laser scanning microscope, FIG. 3(E) presents the fluorescence image illustrating HeLa cells pretreated with the thiol blocker, N-methylmaleimide (NMM), and added with homocysteine and the compound prepared in Example 1, observed under confocal laser scanning microscope, and FIG. 3(F) presents the fluorescence image illustrating HeLa cells pretreated with the thiol blocker, N-methylmaleimide (NMM), and added with glutathione and the compound prepared in Example 1, observed under confocal laser scanning microscope.

As shown in FIG. 3(A) and FIG. 3(B), when HeLa cells were observed under confocal laser scanning microscope, the red fluorescence was not detected. However, when the compound prepared in Example 1 was added to HeLa cells, the strong red fluorescence was detected by confocal laser scanning microscope, suggesting that the compound prepared in Example 1 reacted to the endogenous amino acids containing thiol group (R—SH) such as cysteine, homocysteine, and glutathione.

As shown in FIG. 3(C), the compound prepared in Example 1 was added to HeLa cells pre-treated with the thiol blocker N-methylmaleimide (NMM), followed by observation under confocal laser scanning microscope. As a result, those endogenous amino acids containing thiol group (R—SH) such as cysteine, homocysteine, and glutathione, were inhibited by the thiol blocker NMM, which means there were no amino acids for the compound of Example 1 to react with, so that the red fluorescence was not observed. However, as shown in FIG. 3(D), FIG. 3(E), and FIG. 3(F), when cysteine, homocysteine, and glutathione, were additionally added thereto, which means there were now those amino acids containing thiol group (R—SH) in the cytoplasm for the compound of Example 1 to react, so that the strong red fluorescence was observed.

Therefore, the compound prepared in Example 1 was confirmed to be able to react to those amino acids containing thiol group (R—SH) such as cysteine, homocysteine, and glutathione, in the cytoplasm of HeLa cells, so that it could be effectively used for the detection of the intracellular amino acids containing thiol group (R—SH).

Experimental Example 3: Evaluation of the Glutathione Selectivity 1

The following experiment was performed to evaluate the glutathione selectivity of the compound prepared in Example 2.

10 μM of the compound prepared in Example 2 was treated to HEPES (4-(2-hydroxyethyl)piperazine-1-ethanesulfonic acid) buffer (10 mM, pH=7.4) containing 10% DMSO and 100 μM of each glutathione, cysteine, homocysteine, dithiothreitol, phenylalanine, histidine, glutamine, lysine, glutamate, glycine, serine, alanine, arginine, methionine, and tyrosine, followed by observation of fluorescence spectrum at 25° C. by using RF-5310/PC fluorescence spectrometer (Shimada, 1 cm quartz cell). The results are shown in FIG. 4 and FIG. 5.

FIG. 4 presents the image of fluorescence spectrum generated when the compound prepared in Example 2 and various in vivo amino acids were added respectively to HEPES (4-(2-hydroxyethyl)piperazine-1-ethanesulfonic acid) buffer containing 10% dimethylsulfoxide (DMSO), and FIG. 5 presents the image illustrating the increase of fluorescence strength around 736 nm over the time after the compound prepared in Example 2 and glutathione, cysteine, and homocysteine were added to HEPES (4-(2-hydroxyethyl)piperazine-1-ethanesulfonic acid) buffer containing 10% dimethylsulfoxide (DMSO).

As shown in FIG. 4, the compound prepared in Example 2 selectively reacted to glutathione only with presenting a strong fluorescence strength near 735 nm. However, the reaction to other amino acids was weak so that a very weak fluorescence strength was observed at 736 nm.

As shown in FIG. 5, the compound prepared in Example 2 selectively reacted to glutathione alone among those amino acids containing thiol group (R—SH) such as cysteine, homocysteine, and glutathione, so that it produced a strong fluorescence signal at around 736 nm.

Therefore, the compound prepared in Example 2 could be efficiently used for the detection of glutathione in biosamples because the compound could selectively react to glutathione only among other amino acids containing thiol group (R—SH) such as cysteine, homocysteine, and glutathione.

Experimental Example 4: Observation of Absorption and Fluorescence Spectrum According to the Concentration of Glutathione 1

The following experiment was performed to observe absorption and fluorescence produced by the compound prepared in Example 2 according to the concentration of glutathione (GSH).

<4-1> Observation of Absorption Spectrum

10 μM of the compound prepared in Example 2 and glutathione were added to HEPES (4-(2-hydroxyethyl)piperazine-1-ethanesulfonic acid) buffer (10 mM, pH=7.4) containing 10% dimethylsulfoxide (DMSO) with raising slowly the concentration of glutathione from 0 to 50 μM, during which the changes of absorption spectrum were observed using UV-vis sepctra (Scinco 3000 spectrophotometer, 1 cm quartz cell) at 25° C. The results are shown in FIG. 6.

FIG. 6 presents the image of absorption spectrum that has changed after the compound prepared in Example 2 was added to HEPES (4-(2-hydroxyethyl)piperazine-1-ethanesulfonic acid) buffer containing 10% dimethylsulfoxide (DMSO) with slowly raising the concentration of glutathione therein from 0 to 50 µM.

As shown in FIG. 6, when glutathione was not added, only a weak absorption strength was observed at 750 nm. However, when the concentration of glutathione was slowly raised from 0 to 50 µM, the absorption signal was also getting stronger at 750 nm.

<4-2> Observation of Fluorescence Spectrum

The following experiment was performed by the same manner as described in Experimental Example <4-1> except that fluorescence spectrum was observed by using RF-5310/PC fluorescence spectrometer (Shimada, 1 cm quartz cell) instead of observing absorption spectrum via UV-vis sepctra (Scinco 3000 spectrophotometer, 1 cm quartz cell) ($\lambda_{ex}$=730 nm, $\lambda_{em}$=736 nm, slit:10/10 nm). The results are shown in FIG. 7.

FIG. 7 presents the image of fluorescence spectrum that has changed after the compound prepared in Example 2 was added to HEPES (4-(2-hydroxyethyl)piperazine-1-ethanesulfonic acid) buffer (10 mM, pH=7.4) containing 10% dimethylsulfoxide (DMSO) with slowly raising the concentration of glutathione therein from 0 to 50 µM.

As shown in FIG. 7, when glutathione was not added, only a weak fluorescence signal was observed at 736 nm. However, when the concentration of glutathione was slowly raised from 0 to 50 µM, the fluorescence signal was also getting stronger at 736 nm.

Therefore, it was confirmed that the reaction of the compound prepared in Example 2 was glutathione dose-dependent.

Experimental Example 5: Observation of Absorption and Fluorescence Spectrum Over the time The reaction between glutathione and the compound prepared in Example 2 was induced. Then, the following experiment was performed to observe absorption and fluorescence spectrum over the time.

<5-1> Observation of Absorption Spectrum

10 µM of the compound prepared in Example 2 and 100 µM of glutathione were added to HEPES (4-(2-hydroxyethyl)piperazine-1-ethanesulfonic acid) buffer (10 mM, pH=7.4) containing 10% dimethylsulfoxide (DMSO), followed by observation of absorption spectrum at 25° C. using UV-vis sepctra (Scinco 3000 spectrophotometer, 1 cm quartz cell) over the time. The results are shown in FIG. 8 (spectrum was photographed every 0.5 minute).

FIG. 8 presents the image of absorption spectrum that has changed over the time after the compound prepared in Example 2 and glutathione were added to HEPES (4-(2-hydroxyethyl)piperazine-1-ethanesulfonic acid) buffer containing 10% dimethylsulfoxide (DMSO).

As shown in FIG. 8, when the compound prepared in Example 2 and glutathione were added to the buffer, the minimum absorption signal was observed at 750 nm within 15 minutes.

<5-2> Observation of Fluorescence Spectrum

The following experiment was performed by the same manner as described in Experimental Example <5-1> except that fluorescence spectrum was observed by using RF-5310/PC fluorescence spectrometer (Shimada, 1 cm quartz cell) instead of observing absorption spectrum via UV-vis sepctra (Scinco 3000 spectrophotometer, 1 cm quartz cell) ($\lambda_{ex}$=730 nm, $\lambda_{em}$=736 nm, slit:10/10 nm). The results are shown in FIG. 9 (spectrum was photographed every 0.5 minute).

FIG. 9 presents the image of fluorescence spectrum that has changed over the time after the compound prepared in Example 2 and glutathione were added to HEPES (4-(2-hydroxyethyl)piperazine-1-ethanesulfonic acid) buffer containing 10% dimethylsulfoxide (DMSO).

As shown in FIG. 9, when the compound prepared in Example 2 and glutathione were added to the buffer, the maximum fluorescence signal was observed at 736 nm within 15 minutes.

Therefore, it was confirmed that the compound prepared in Example 2 reacted to glutathione so as to produce absorption or fluorescence spectrum fast.

Experimental Example 6: Mechanism of the Reaction with Glutathione

To understand the reaction mechanism between the compound prepared in Example 2 and glutathione, matrix assisted laser desorption/ionization time-of-flight mass spectrometry was performed to induce the reaction between glutathione and the compound prepared in Example 2. The results are shown in FIG. 10.

FIG. 10 presents the image obtained from matrix assisted laser desorption/ionization time-of-flight mass spectrometry performed after the reaction between glutathione and the compound prepared in Example 2.

As shown in FIG. 10, the compound prepared in Example 2 reacted to glutathione, so that sulfonyl-N,N-dimethylnaphthalene-1-amine group in the compound of Example 2 was fallen apart to produce cyanine derivative (A) having free piperazine (589.1 m/z). Particularly, in the molecular structure of the sulfonyl-N,N-dimethylnaphthalene-1-amine group fallen apart therefrom, N,N-dimethylnaphthalene-1-amine group was conjugated with thiol group in glutathione to produce another compound (B) (477.5 m/z).

From the above results, it was confirmed that the changes of absorption or fluorescence spectrum produced by the reaction between the compound of the invention based on cyanine scaffold and glutathione were attributed to the reaction presented in FIG. 10.

Experimental Example 7: Evaluation of the Detection of Intracellular Biothiol 2

The following experiment was performed to evaluate the selective detection capacity of the compound prepared in Example 2 for cysteine, homocysteine, and glutathione, among many biothiols that are the amino acids containing thiol group (R—SH).

HeLa cells (human adenocarcinoma cells, Korea Cell Line Bank) were cultured in RPMI 1640 (Roswell Park Memorial Institute) supplemented with 10% heat-inactivated fetal bovine serum (FBS), 100 U/mL penicillin, and 100 U/mL streptomycin in a 37° C. 5% $CO_2$ incubator. The cells were either treated or not treated with 1 mM of N-methylmaleimide (NMM) known as a thiol blocker for 20 minutes. 100 µM of each amino acid containing thiol group (R—SH) such as cysteine, homocysteine, and glutathione was added thereto. Then, the cells were seeded in 35-mm glass bottomed dishes at the density of $3\times10^5$ cells/dish in 1640 medium. 24 hours later, 10 µM of the compound prepared in Example 1 was added thereto, followed by culture at 37° C. for 20 minutes. The cells were washed with DPBS (Dulbecco's Phosphate Buffered Saline) twice to eliminate the remaining compound, followed by imaging with confocal laser scanning microscope (Fluoview 1200, Olympus, Japan). At this time, the emitting filter with the excitation wavelength of 635 nm and the band-path (BP) of 655~755 nm was used. The results are shown in FIG. 11.

FIG. 11(A) presents the fluorescence image illustrating HeLa cells observed under confocal laser scanning microscope, FIG. 11(B) presents the fluorescence image illustrating HeLa cells added with the compound prepared in Example 2, observed under confocal laser scanning microscope, FIG. 11(C) presents the fluorescence image illustrating HeLa cells pretreated with the thiol blocker, N-methylmaleimide (NMM), and added with the compound prepared in Example 2, observed under confocal laser scanning microscope, FIG. 11(D) presents the fluorescence image illustrating HeLa cells pretreated with the thiol blocker, N-methylmaleimide (NMM), and added with cysteine and the compound prepared in Example 2, observed under confocal laser scanning microscope, FIG. 11(E) presents the fluorescence image illustrating HeLa cells pretreated with the thiol blocker, N-methylmaleimide (NMM), and added with homocysteine and the compound prepared in Example 2, observed under confocal laser scanning microscope, and FIG. 11(F) presents the fluorescence image illustrating HeLa cells pretreated with the thiol blocker, N-methylmaleimide (NMM), and added with glutathione and the compound prepared in Example 2, observed under confocal laser scanning microscope.

As shown in FIG. 11(A) and FIG. 11(B), when HeLa cells were observed under confocal laser scanning microscope, the red fluorescence was not detected. On the other hand, when the compound of example 2 was added to HeLa cells, the strong red fluorescence was observed under confocal laser scanning microscope, suggesting that the compound of Example 2 reacted to glutathione.

As shown in FIG. 11(C), the compound prepared in Example 2 was added to HeLa cells pre-treated with the thiol blocker N-methylmaleimide (NMM), followed by observation under confocal laser scanning microscope. As a result, those endogenous amino acids containing thiol group (R—SH) such as cysteine, homocysteine, and glutathione, were inhibited by the thiol blocker NMM, which means there were no amino acids for the compound of Example 2 to react to, so that the red fluorescence was not observed. As shown in FIG. 11(D) and FIG. 11(E), when cysteine and homocysteine were additionally added thereto, the compound prepared in Example 2 did not react to those amino acids containing thiol group (R—SH), which were cysteine and homocysteine, so that the red fluorescence was not detected. In the meantime, glutathione was additionally added thereto, as shown in FIG. 11(F), the strong red fluorescence was observed, suggesting that the compound prepared in Example 2 reacted selectively to glutathione.

The compound prepared in Example 2 reacted selectively to glutathione alone among the amino acids containing thiol group (R—SH) such as cysteine, homocysteine, and glutathione, etc, in the cytoplasm of HeLa cells, confirmed by the strong red fluorescence detected under confocal laser scanning microscope. Therefore, the compound of Example 2 can be efficiently used for the selective detection of glutathione.

Experimental Example 8: Observation of the Changes of the Concentration of Glutathione According to the Presence of an Oxidant 1

100 μM of $H_2O_2$, the oxidant, was treated to HeLa cells prepared in Experimental Example 2 containing glutathione, the anti-oxidant, at 37° C. for 30 minutes to induce the changes of glutathione level. 20 μM of the compound prepared in Example 2 was added thereto, followed by culture at 37° C. for 20 minutes. The cells were washed with DPBS (Dulbecco's Phosphate Buffered Saline) three times to eliminate the remaining compound, followed by imaging with confocal laser scanning microscope (Fluoview 1200, Olympus, Japan). At this time, the emitting filter with the excitation wavelength of 635 nm and the band-path (BP) of 655~755 nm was used. The results are shown in FIG. 12.

Figure 12B:
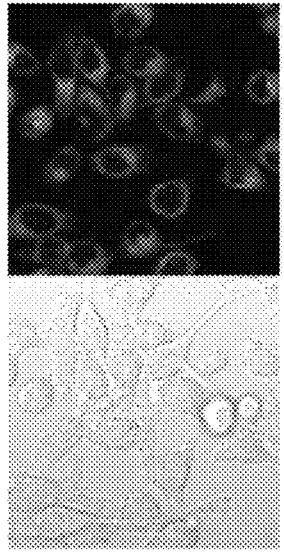
FIG. 12(B) presents the fluorescence image illustrating HeLa cells added with the compound prepared in Example 2, observed under confocal laser scanning microscope.
Figure 12C:
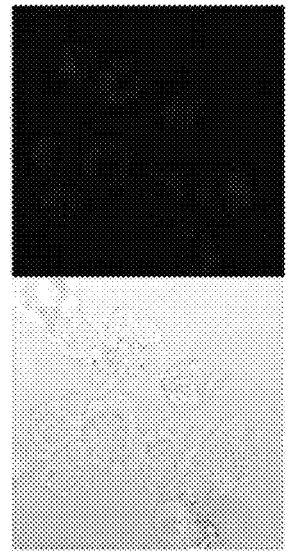
FIG. 12(C) presents the fluorescence image illustrating HeLa cells pretreated with $H_2O_2$, and added with the compound prepared in Example 2, observed under confocal laser scanning microscope.

FIG. 12(A) presents the fluorescence image illustrating HeLa cells observed under confocal laser scanning microscope, FIG. 12(B) presents the fluorescence image illustrating HeLa cells added with the compound prepared in Example 2, observed under confocal laser scanning microscope, and FIG. 12(C) presents the fluorescence image illustrating HeLa cells pretreated with $H_2O_2$, and added with the compound prepared in Example 2, observed under confocal laser scanning microscope.

As shown in FIG. 12(A) and FIG. 12(B), when HeLa cells were observed under confocal laser scanning microscope, the red fluorescence was not detected. In the meantime, when the compound prepared in Example 2 was added thereto, the compound prepared in Example 2 reacted to glutathione, so that it produced a strong red fluorescence under confocal laser scanning microscope.

Also, as shown in FIG. 12(C), the compound prepared in Example 2 was added to HeLa cells pre-treated with $H_2O_2$, followed by observation under confocal laser scanning microscope. As a result, the anti-oxidant glutathione was oxidized by the oxidant ($H_2O_2$), so that the compound prepared in Example 2 lost a target to react, that was glutathione, in HeLa cells. Therefore, the red fluorescence was not observed. In general, glutathione reacts to an endogenous oxidant and is converted into the reversible glutathione disulfide (GSSG) which is the oxidized glutathione wherein two glutathione molecules are conjugated each other via disulfide bond (—S—S—). By such reaction, in vivo oxidation-reduction potential is regulated.

Therefore, the compound prepared in Example 2 could be used for measuring the concentration of glutathione by detecting the strength of red fluorescence and was also confirmed to have excellent selectivity to glutathione since it did not react to the oxidized glutathione, glutathione disulfide (GSSG).

Experimental Example 9: Observation of the Changes of the Concentration of Glutathione According to the Presence of an Oxidant 2

RAW 264.7 cells (macrophage cell line, Korea Cell Line Bank) were cultured in RPMI 1640 (Roswell Park Memorial Institute) supplemented with 10% heat-inactivated fetal bovine serum (FBS), 100 U/mL penicillin, and 100 U/mL streptomycin in a 37° C. 5% $CO_2$ incubator.

RAW 264.7 cells displaying the characteristics of generating ROS (Reactive Oxygen Species) or RNS (Reactive Nitrogen Species) were treated with 1 μg/mL of lipopolysaccharide (LPS) for 20 minutes, 50 ng/mL of interferon-γ for 16 hours, and 20 μM of phorbol 12-myristate 13-acetate (PMA) for 20 minutes in order to induce the generation of endogenous feroxynitrite having the characteristics of an oxidant. Then, the cells were seeded in 35-mm glass bottomed dishes at the density of $3\times10^5$ cells/dish in 1640 medium. 24 hours later, the compound prepared in Example 2 was treated thereto at the concentration of 20 μM for 20 minutes. The cells were washed with DPBS (Dulbecco's Phosphate Buffered Saline) three times, followed by imaging with confocal laser scanning microscope (Fluoview 1200, Olympus, Japan). At this time, the emitting filter with the excitation wavelength of 635 nm and the band-path (BP) of 655~755 nm was used. The results are shown in FIG. 13.

Figure 13A:
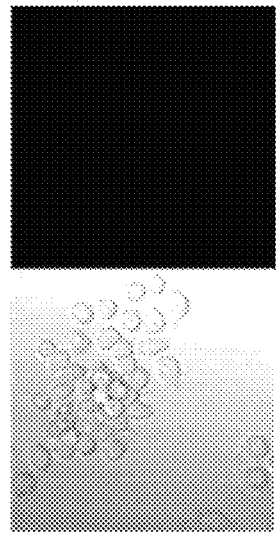
FIG. 13(A) presents the fluorescence image illustrating RAW 264.7 cells observed under confocal laser scanning microscope.
Figure 13B:
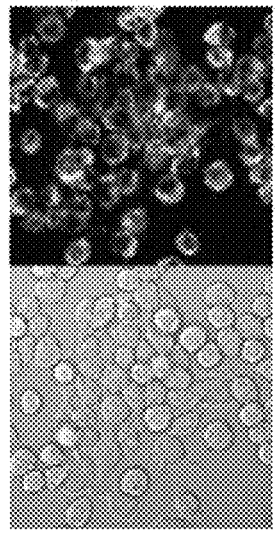
FIG. 13(B) presents the fluorescence image illustrating RAW 264.7 cells added with the compound prepared in Example 2, observed under confocal laser scanning microscope.
Figure 13C:
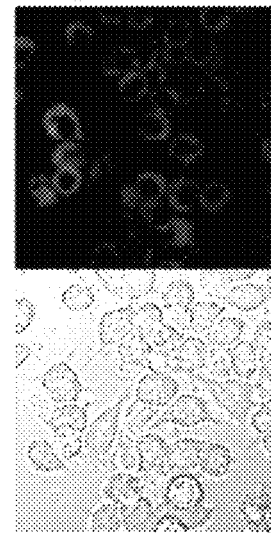
FIG. 13(C) presents the image of RAW 264.7 cells wherein the production of peroxynitrite, the oxidant, was induced to reduce glutathione and then the compound prepared in Example 2 was treated thereto, obtained by confocal laser scanning microscope.

FIG. 13(A) presents the fluorescence image illustrating RAW 264.7 cells observed under confocal laser scanning microscope, FIG. 13(B) presents the fluorescence image illustrating RAW 264.7 cells added with the compound prepared in Example 2, observed under confocal laser scanning microscope, and FIG. 13(C) presents the image of RAW 264.7 cells wherein the production of peroxynitrite, the oxidant, was induced to reduce glutathione and then the compound prepared in Example 2 was treated thereto, obtained by confocal laser scanning microscope.

As shown in FIG. 13(A) and FIG. 13(B), when RAW 264.7 cells were observed under confocal laser scanning microscope, the red fluorescence was not detected. In the meantime, when the compound prepared in Example 2 was added thereto, the compound prepared in Example 2 reacted to glutathione, so that it produced a strong red fluorescence under confocal laser scanning microscope.

Also, as shown in FIG. 13(C), the compound prepared in Example 2 was added to RAW 264.7 cells pre-treated with peroxynitrite, followed by observation under confocal laser scanning microscope. As a result, the anti-oxidant glutathione was oxidized by the oxidant (peroxynitrite), so that the compound prepared in Example 2 lost a target to react, that was glutathione, in RAW 264.7 cells. Therefore, the red fluorescence was not observed. In general, glutathione reacts to an endogenous oxidant and is converted into the reversible glutathione disulfide (GSSG) which is the oxidized glutathione wherein two glutathione molecules are conjugated each other via disulfide bond (—S—S—). By such reaction, in vivo oxidation-reduction potential is regulated.

Therefore, the compound prepared in Example 2 could be used for measuring the concentration of glutathione by detecting the strength of red fluorescence and was also confirmed to have excellent selectivity to glutathione since it did not react to the oxidized glutathione, glutathione disulfide (GSSG).

Experimental Example 10: Evaluation of the Detection of Glutathione by Using a Mouse Model 1

The following experiment was performed to evaluate the glutathione detection capacity of the compound prepared in Example 2 by using a mouse model.

200 µL of HEPES (4-(2-hydroxyethyl)piperazine-1-ethanesulfonic acid) buffer (10 mM, pH=7.4) containing 20 mM of N-methylmaleimide (NMM) known as a thiol blocker was administered to each C57BL/6 mouse (7~8 weeks old, female, Jackson Laboratory) via intravenous injection. 20 minutes later, 200 µL of HEPES (4-(2-hydroxyethyl)piperazine-1-ethanesulfonic acid) buffer (10 mM, pH=7.4) containing 50 mM of the compound prepared in Example 2 was administered to the mouse via intravenous injection. 20 minutes later, the strength of fluorescence was observed by using the epifluorescence mode of In Vivo Imaging System (IVIS) spectrum (Caliper LifeSciences, USA) equipped with the filter having the wavelengths of 675 nm and 720 nm [the strength of fluorescence was measured by Living Image Software 4.3.1 (Caliper Life Sciences, USA)]. The results are shown in FIG. 14 and FIG. 15.

FIG. 14(A) presents the image of the mouse treated with nothing, obtained by in vivo imaging system (IVIS) spectrum, FIG. 14(B) presents the image of the mouse treated with N-methylmaleimide (NMM), obtained by in vivo imaging system (IVIS) spectrum, FIG. 14(C) presents the image of the mouse treated with the compound prepared in Example 2, obtained by in vivo imaging system (IVIS) spectrum, FIG. 14(D) presents the image of the mouse treated with N-methylmaleimide (NMM) and the compound prepared in Example 2, obtained by in vivo imaging system (IVIS) spectrum, FIG. 15(A) presents the image of livers of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum, FIG. 15(B) presents the image of kidneys of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum, FIG. 15(C) presents the image of lungs of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum, and FIG. 15(D) presents the image of spleens of the mouse treated with nothing, the mouse treated with N-methylmaleimide (NMM), the mouse treated with the compound prepared in Example 2, and the mouse treated with the compound prepared in Example 2 and N-methylmaleimide (NMM) together, obtained by in vivo imaging system (IVIS) spectrum As shown in FIG. 14(A) and FIG. 14(B), the strength of fluorescence generated from the mouse treated with nothing was equal to that of the mouse treated with N-methylmaleimide (NMM), indicating that the changes of glutathione level could not be observed. In the meantime, as shown in FIG. 14(C), in the mouse treated with the compound prepared in Example 2, the compound was introduced in the organ through blood stream where glutathione exists and reacted to glutathione therein, so that a strong red fluorescence was observed. In addition, as shown in FIG. 14(D), in the mouse treated with N-methylmaleimide (NMM) together with the compound of Example 2, glutathione in the organ was inhibited by NMM, so that the red fluorescence was not observed.

As shown in FIGS. 15(A)~15(D), the distribution of fluorescence signal in the liver, kidney, lung, and spleen of the mouse treated with nothing was equally observed in that of the mouse treated with methylmaleimide (NMM), suggesting that the changes of glutathione level were not observed. On the other hand, in the mouse treated with the compound prepared in Example 2, the compound flew through blood stream and reacted to glutathione in the liver, kidney, lung, and spleen of the mouse, so that a strong red fluorescence was observed. In the mouse treated with N-methylmaleimide (NMM) together with the compound of Example 2, glutathione in the liver, kidney, lung, and spleen was inhibited by NMM, so that the red fluorescence was not observed.

Therefore, it was confirmed that the compound prepared in Example 2 could be efficiently used for the observation of in vivo glutathione distribution by detecting the red fluorescence observed from In Vivo Imaging System (IVIS) spectrum.

Experimental Example 10: Evaluation of the Detection of Glutathione by Using a Mouse Model 2

The following experiment was performed to evaluate the glutathione detection capacity of the compound prepared in Example 2 by using a mouse model.

200 µL of HEPES (4-(2-hydroxyethyl)piperazine-1-ethanesulfonic acid) buffer (10 mM, pH=7.4) containing 300 mg/kg of acetaminophen (APAP) known as a pain killer was administered to each C57BL/6 mouse (7~8 weeks old, female, Jackson Laboratory) via intravenous injection. The said APAP works as a pain killer in vivo when administered at a proper dose, but when treated at over-dose, it can damage organs and also reduce in vivo glutathione. 20 minutes later, 200 µL of HEPES (4-(2-hydroxyethyl)piperazine-1-ethanesulfonic acid) buffer (10 mM, pH=7.4) containing 50 mM of the compound prepared in Example 2 was administered to the mouse via intravenous injection. 20 minutes later, the strength of fluorescence was observed by using the epifluorescence mode of In Vivo Imaging System (IVIS) spectrum (Caliper LifeSciences, USA) equipped with the filter having the wavelengths of 675 nm and 720 nm [the strength of fluorescence was measured by Living Image Software 4.3.1 (Caliper Life Sciences, USA)]. The results are shown in FIG. 16 and FIG. 17.

FIG. 16(A) presents the image of the mouse treated with the compound prepared in Example 2, obtained by in vivo imaging system (IVIS) spectrum, FIG. 16(B) presents the image of the mouse treated with acetaminophen (APAP) and the compound prepared in Example 2 together, obtained by in vivo imaging system (IVIS) spectrum, FIG. 17(A) presents the image of livers of the mouse treated with the compound prepared in Example 2 and the mouse treated with acetaminophen (APAP) and the compound prepared in Example 2 together, obtained by in vivo imaging system (IVIS) spectrum, FIG. 17(B) presents the image of kidneys of the mouse treated with the compound prepared in Example 2 and the mouse treated with acetaminophen (APAP) and the compound prepared in Example 2 together, obtained by in vivo imaging system (IVIS) spectrum, FIG. 17(C) presents the image of lungs of the mouse treated with the compound prepared in Example 2 and the mouse treated with acetaminophen (APAP) and the compound prepared in Example 2 together, obtained by in vivo imaging system (IVIS) spectrum, and FIG. 17(D) presents the image of spleens of the mouse treated with the compound prepared in Example 2 and the mouse treated with acetaminophen (APAP) and the compound prepared in Example 2 together, obtained by in vivo imaging system (IVIS) spectrum.

As shown in FIG. 16(A), in the mouse treated with the compound prepared in Example 2, the compound was introduced via blood stream in the organs harboring glutathione, and reacted therein to glutathione, so that a strong red fluorescence was observed. In the meantime, as shown in FIG. 16(B), in the mouse treated with acetaminophen (APAP) together with the compound of Example 2, glutathione in the organ was inhibited by APAP, so that the red fluorescence was not observed.

As shown in FIGS. 17(A)~17(D), in the mouse treated with the compound prepared in Example 2, the compound flew through blood stream and reacted to glutathione in the liver, kidney, lung, and spleen of the mouse, so that a strong red fluorescence was observed. On the other hand, in the mouse treated with acetaminophen (APAP) together with the compound of Example 2, glutathione in the liver, kidney, lung, and spleen was inhibited by APAP, so that the red fluorescence was not observed.

Therefore, it was confirmed that the compound prepared in Example 2 could be efficiently used for the observation of in vivo glutathione distribution by detecting the red fluorescence observed from In Vivo Imaging System (IVIS) spectrum.

Experimental Example 12: Evaluation of the Capacity of Diagnosing Sepsis 1

The following experiment was performed to evaluate the capacity of diagnosing sepsis of the compound prepared in Example 2.

According to a reference (J Vis Exp. 2011 May 7; (51). pii: 2860. doi: 10.3791/2860), C57BL/6 mouse (7~8 weeks old, female, Jackson Laboratory) was induced with sepsis by performing CLP (cecal ligation and puncture). 8 hours later, peritoneal cells were extracted from the mouse. The cells were centrifuged and reacted to the neutrophil marker Ly6G (eFluor®450, eBioscience, Cat No. 48-5931) and 10 µM of the compound prepared in Example 2 at room temperature. 25 minutes later, 1 mL of 3% fetal bovine serum (FBS) was added thereto, followed by centrifugation at 3000 rpm for 5 minutes to wash the cells. The cells were resuspended in 200 mL of HEPES (4-(2-hydroxyethyl)piperazine-1-ethanesulfonic acid) buffer (10 mM, pH=7.4), followed by FACS (Fluorescence Activated Cell Sorting) using the data analysis software FlowJo to observe the peaks (The setting for Alexa flour 700 fluorescence was hired, BD FACSVerse™). The results are shown in FIG. 18.

FIG. 18 presents the image indicating the concentration of glutathione in neutrophils of peritoneal cells of the mouse induced with sepsis and of the normal mouse, obtained by FACS (Fluorescence Activated Cell Sorting).

As shown in FIG. 18, the glutathione level was reduced in the mouse induced with sepsis, compared with that of the normal mouse. In general, sepsis causes oxidative stress in neutrophils, and as a result ROS (reactive oxygen species) is excessively generated. This excessive ROS causes disorders in neuron, skin, and digestive system, etc. Glutathione that is an antioxidant capable of regulating oxidation/reduction potential reacts to the excessive ROS generated by sepsis, so that it can be converted to reversible glutathione disulfide (GSSG), that is an oxidized glutathione. Therefore, the concentration of GSH was reduced in the mouse induced with sepsis.

From the above experiment, it was confirmed that the compound prepared in Example 2 could be efficiently used for the diagnosis of sepsis by measuring the concentration of glutathione.

Experimental Example 13: Evaluation of the Capacity of Diagnosing Sepsis 2

The following experiment was performed to evaluate the capacity of diagnosing sepsis of the compound prepared in Example 2.

Neutrophils were extracted from the bone marrow of C57BL/6 mouse (7~8 weeks old, female, Jackson Laboratory). The cells were infected with green fluorescent protein (GFP) tagged *Pseudomonas Aeruginosa* 01 (PA01) that is the causing bacteria of sepsis. 24 hours later, 10 μM of the compound prepared in Example 2 was added thereto, followed by reaction at 37° C. for 20 minutes. At this time, the emitting filter with the excitation wavelength of 635 nm and the band-path (BP) of 655~755 nm was used. The results are shown in FIG. 19.

FIG. 19 presents the fluorescence image of neutrophils, which were infected with green fluorescent protein tagged *Pseudomonas aeruginosa*, of the mouse treated with the compound prepared in Example 2, obtained by confocal laser scanning microscope.

As shown in FIG. 19, when the neutrophils were treated with nothing, neither red fluorescence nor green fluorescence was detected. In the meantime, when the neutrophils were infected with green fluorescent protein tagged PA01, a strong green fluorescence was observed in the green fluorescent channel because of the green fluorescent protein tagged to PA01. Also, when the compound prepared in Example 2 was treated to the neutrophils not-infected with green fluorescent protein tagged PA01, a strong red fluorescence was detected in the red fluorescent channel.

After infecting the neutrophils with green fluorescent protein tagged PA01, the neutrophils were treated with the compound prepared in Example 2. At this time, the neutrophils got oxidative stress so that the cells produced ROS (Reactive Oxygen Species) excessively. As described in Experimental Example 12, glutathione reacted to ROS to generate glutathione disulfide (GSSG), resulting in the decrease of glutathione. Therefore, a red fluorescence indicating glutathione level was reduced in the red fluorescence channel.

Therefore, it was confirmed that the compound prepared in Example 2 could be efficiently used for the diagnosis of sepsis by measuring the concentration of glutathione.

Experimental Example 14: Investigation of the Structure of the Compound and Measurement of Band-Gap To investigate the glutathione specific selectivity of the compound prepared in Example 2, the following experiment was performed.

First, as shown in FIG. 20, the compound prepared in Example 2 was fragmented into two fragments containing piperazine.

FIG. 20 presents the image illustrating two fragments of the compound prepared in Example 2 that contained piperazine The fragment 1 of FIG. 20 was prepared according to a reference (Kim, J.; Lim, S.-H.; Yoon, Y.; Thangadurai, T. D.; Yoon, S. Tetrahedron Lett. 2011, 52, 2645), and the fragment 2 was the compound prepared in step 1) of Example 1 of the invention.

An experiment was performed by the same manner as described in Experimental Example 3 except that the fragment 1 or the fragment 2 was used instead of the compound prepared in Example 2. As a result, no changes in absorption or fluorescence spectrum were detected. From the above results, it was confirmed that the fragment 1 or the fragment 2 originated from the compound prepared in Example 2 did not have the capacity of detecting glutathione. To disclose the reason in relation to the above, the 3-dimensional structure of each of the compound of Example 1, the compound of Example 2, and the fragment 1 or the fragment 2, was investigated along with band-gap.

To investigate the 3-dimensional structure and band-gap of the compounds, an experiment was performed based on Density Function Theory (DFT) at the level of B3LYP/6-31G* using Gaussian 09 program. The results are shown in FIG. 21 and FIG. 22.

FIG. 21 presents the image illustrating three-dimensional structures of the compound of Example 1, the compound of Example 2, the compound fragment 1, and the compound fragment 2, analyzed based on DFT (Density Function Theory) at the level of B3LYP/6-31G* using Gaussian 09 program. (A) possible conformation of piperazine; (B) fragment 1; (C) fragment 2; (D) compound of example 2; (E) compound of example 1, FIG. 22 presents the image illustrating the band-gap among the compound of Example 1, the compound of Example 2, and the compound fragment 2 analyzed based on DFT (Density Function Theory) at the level of B3LYP/6-31G* using Gaussian 09 program As shown in FIG. 21(A), piperazine could exist in the forms of boat conformation, twist-boat conformation, and chair conformation. As shown in FIG. 21(B), piperazine of the fragment 1 compound was in the form of twist-boat conformation. As shown in FIG. 21(C), piperazine of the fragment 2 compound was in the form of chair conformation. As shown in FIG. 21(D), piperazine of the compound prepared in Example 2 was in the form of chair conformation, like piperazine of the fragment 2 compound, and as shown in FIG. 21(E), piperazine of the compound prepared in Example 1 was in the form of twist-boat conformation.

Unlike the expectation that the conformation of piperazine could affect the selectivity, piperazine of the compound prepared in Example 2 showing glutathione specific selectivity and piperazine of the fragment 2 compound having no glutathione specific selectivity (compound of step 1 of Example 1) were equally in the form of chair conformation.

When the compound prepared in Example 2 reacted to glutathione, as the reaction progressed as shown in FIG. 10, binding mode of active site where reaction progressed was observed. As a result, hydrogen atom of —NH— in piperazine of the fragment 2 compound (compound of step 1 of Example 1) was in the form of a-binding, while dansyl group binding to piperazine of the compound prepared in Example 2 was in the form of e-binding.

Under the presumption that the length of S—N bond in the compounds of Example 1, Example 2, and the fragment 1 could affect the glutathione specific selectivity, the length of S—N bond was measured. As a result, the length of S—N bond of the compound of Example 1 and the fragment 1 compound was respectively 1,667 Å and 1,660 Å. In the meantime, the length of S—N bond in the compound prepared in Example 2 was 1,727 Å, suggesting that the binding energy of the compound prepared in Example 2 was smaller than that of the compound prepared in Example 1 and the fragment 1 compound, so that the bond in the compound of Example 2 could be broken more easily.

Further, as shown in FIG. 22, band-gaps of the compounds of Example 1, Example 2, and fragment 2 were respectively 2.14 eV, 2.13 eV, and 2.22 eV according to the different functional group introduced in piperazine. The compounds of Example 1 and Example 2 having comparatively smaller band-gap were therefore expected to be useful as a near infrared fluorescent dye.

In conclusion, the selectivity of the compound prepared in Example 2 was attributed to the conformation of piperazine in the active site where the reaction to glutathione progressed, the conformation of dansyl group that is binding to piperazine, the length of S—N bond, and the band-gap energy.

Experimental Example 15: Evaluation of the Glutathione Selectivity 2

The following experiment was performed to evaluate the glutathione (GSH) selectivity of the compound prepared in Example 3.

<15-1> Observation of Absorption Spectrum

10 μM of the compound prepared in Example 3 and 100 μM of each endogenous amino acid (alanine, arginine, cysteine, glutamate, glycine, glutathione, homocysteine, histidine, lysine, methionine, serine, and tyrosine) were added to HEPES (4-(2-hydroxyethyl)piperazine-1-ethanesulfonic acid) buffer (10 mM, pH=7.4) containing 10% dimethylsulfoxide (DMSO), followed by observation of absorption spectrum presented through UV-vis sepctra (Scinco 3000 spectrophotometer, 1 cm quartz cell) at 25° C. The results are shown in FIG. 23.

FIG. 23 presents the image of absorption spectrum produced in HEPES (4-(2-hydroxyethyl)piperazine-1-ethanesulfonic acid) buffer containing 10% dimethylsulfoxide (DMSO) which was added respectively with the compound prepared in Example 3 and various in vivo amino acids.

As shown in FIG. 23, the compound prepared in Example 3 selectively reacted to glutathione only with presenting a weak absorption signal near 830 nm, while other amino acids except glutathione produced a strong absorption signal at 830 nm.

<15-2> Observation of Fluorescence Spectrum

The following experiment was performed by the same manner as described in Experimental Example <15-1> except that fluorescence spectrum was observed by using RF-5310/PC fluorescence spectrometer (Shimada, 1 cm quartz cell) instead of observing absorption spectrum via UV-vis sepctra (Scinco 3000 spectrophotometer, 1 cm quartz cell) ($\lambda_{ex}$=730 nm, $\lambda_{em}$=736 nm, slit:10/10 nm). The results are shown in FIG. 24.

FIG. 24 presents the image of fluorescence spectrum produced in HEPES (4-(2-hydroxyethyl)piperazine-1-ethanesulfonic acid) buffer containing 10% dimethylsulfoxide (DMSO) which was added respectively with the compound prepared in Example 3 and various in vivo amino acids.

As shown in FIG. 24, the compound prepared in Example 3 selectively reacted to glutathione only with presenting a strong fluorescence signal near 780 nm, while other amino acids except glutathione produced a weak fluorescence signal at 780 nm.

Therefore, the compound prepared in Example 3 was confirmed to be efficiently used for the detection of glutathione in biosamples because the compound could selectively react to glutathione only among many other endogenous amino acids to make changes in absorption or fluorescence spectrum.

Experimental Example 16: Observation of Absorption and Fluorescence Spectrum According to the Concentration of Glutathione 2

The following experiment was performed to observe absorption and fluorescence produced by the compound prepared in Example 3 according to the concentration of glutathione (GSH).

<16-1> Observation of Absorption Spectrum

10 μM of the compound prepared in Example 3 and glutathione were added to HEPES (4-(2-hydroxyethyl)piperazine-1-ethanesulfonic acid) buffer (10 mM, pH=7.4) containing 10% dimethylsulfoxide (DMSO) with raising slowly the concentration of glutathione from 0 to 100 μM, during which the changes of absorption spectrum were observed using UV-vis sepctra (Scinco 3000 spectrophotometer, 1 cm quartz cell) at 25° C. The results are shown in FIG. 25.

FIG. 25 presents the image of absorption spectrum that has changed after the compound prepared in Example 3 was added to HEPES (4-(2-hydroxyethyl)piperazine-1-ethanesulfonic acid) buffer containing 10% dimethylsulfoxide (DMSO) with slowly raising the concentration of glutathione therein from 0 to 100 μM.

As shown in FIG. 25, when glutathione was not added, only a strong absorption signal was observed at 830 nm. However, when the concentration of glutathione was slowly raised from 0 to 100 μM, the absorption signal was also getting weaker at 830 nm.

<16-2> Observation of Fluorescence Spectrum

The following experiment was performed by the same manner as described in Experimental Example <16-1> except that fluorescence spectrum was observed by using RF-5310/PC fluorescence spectrometer (Shimada, 1 cm quartz cell) instead of observing absorption spectrum via UV-vis sepctra (Scinco 3000 spectrophotometer, 1 cm quartz cell) ($\lambda_{ex}$=730 nm, $\lambda_{em}$=736 nm, slit:10/10 nm). The results are shown in FIG. 26.

FIG. 26 presents the image of fluorescence spectrum that has changed after the compound prepared in Example 3 was added to HEPES (4-(2-hydroxyethyl)piperazine-1-ethanesulfonic acid) buffer (10 mM, pH=7.4) containing 10% dimethylsulfoxide (DMSO) with slowly raising the concentration of glutathione therein from 0 to 100 μM.

As shown in FIG. 26, when glutathione was not added, only a weak fluorescence signal was observed at 780 nm. However, when the concentration of glutathione was slowly raised from 0 to 100 μM, the fluorescence signal was also getting stronger at 780 nm.

Therefore, it was confirmed that the compound prepared in Example 3 react to glutathione dose-dependently.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:
1. A compound represented by the below formula 1:

[Formula 1]

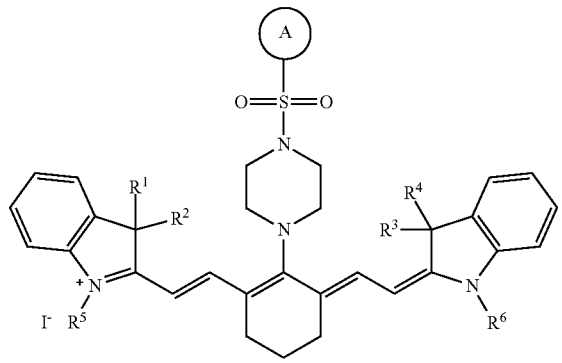

wherein,
$R^1$, $R^2$, $R^3$, $R^4$, $R^5$, and $R^6$ are independently —H, —OH, halogen, $C_{1-10}$ straight or branched alkyl, or $C_{1-10}$ straight or branched alkoxy;

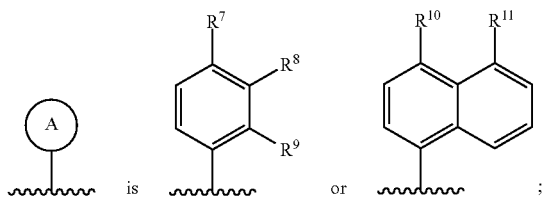

$R^7$, $R^8$, and $R^9$ are independently —H, —OH, —CN, —NO$_2$, halogen, $C_{1-10}$ straight or branched alkyl, or $C_{1-10}$ straight or branched alkoxy;

$R^{10}$ and $R^{11}$ are independently —H, —OH, —CN, —NO$_2$, halogen, $C_{1-10}$ straight or branched alkyl, $C_{1-10}$ straight or branched alkoxy, or —NR$^{12}$R$^{13}$ wherein $R^{12}$ and $R^{13}$ are independently $C_{1-5}$ straight or branched alkyl; or $R^{10}$ and $R^{11}$ can be linked with neighboring carbon atoms and fused with two phenyls, and they can also form non-substituted or substituted 6-atom heterocycloalkyl containing one or more hetero atoms selected from the group consisting of N, O, and S, wherein the substituted 6-atom heterocycloalkyl is one wherein one or more substituents selected from the group consisting of —OH, —CN, —NO$_2$, halogen, =O, $C_{1-10}$ straight or branched alkyl, and $C_{1-10}$ straight or branched alkoxy are substituted.

2. The compound according to claim 1, wherein $R^1$, $R^2$, $R^3$, $R^4$, $R^5$, and $R^6$ are independently —H, $C_{1-10}$ straight or branched alkyl, or $C_{1-10}$ straight or branched alkoxy;

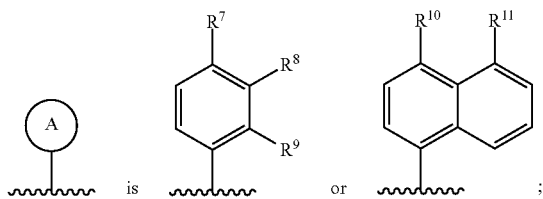

$R^7$, $R^8$, and $R^9$ are independently —H, —NO$_2$, $C_{1-10}$ straight or branched alkyl, or $C_{1-10}$ straight or branched alkoxy;

$R^{10}$ and $R^{11}$ are independently —H, —NO$_2$, $C_{1-10}$ straight or branched alkyl, $C_{1-10}$ straight or branched alkoxy, or —NR$^{12}$R$^{13}$, wherein $R^{12}$ and $R^{13}$ are independently $C_{1-5}$ straight or branched alkyl; or $R^{10}$ and $R^{11}$ can be linked with neighboring carbon atoms and fused with two phenyls, and they can also form non-substituted or substituted 6-atom heterocycloalkyl containing one or more hetero atoms selected from the group consisting of N, O, and S, wherein the substituted 6-atom heterocycloalkyl is the one wherein one or more substituents selected from the group consisting of —NO$_2$, halogen, =O, $C_{1-10}$ straight or branched alkyl, and $C_{1-10}$ straight or branched alkoxy are substituted.

3. The compound according to claim 1, wherein $R^1$, $R^2$, $R^3$, $R^4$, $R^5$, and $R^6$ are independently $C_{1-10}$ straight or branched alkyl;

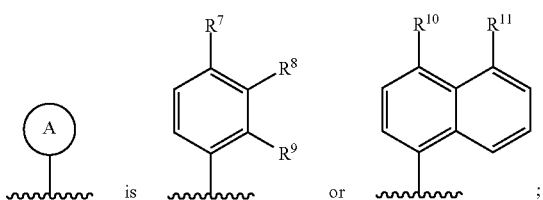

$R^7$, $R^8$, and $R^9$ are independently —H or —NO$_2$;

$R^{10}$ and $R^{11}$ are independently —H or —NR$^{12}$R$^{13}$ wherein $R^{12}$ and $R^{13}$ are independently $C_{1-5}$ straight or branched alkyl; or $R^{10}$ and $R^{11}$ can be linked with neighboring carbon atoms and fused with two phenyls, and they can also form non-substituted or substituted 6-atom heterocycloalkyl containing one or more Ns, wherein the substituted 6-atom heterocycloalkyl is the one wherein one or more substituents selected from the group consisting of =O and $C_{1-10}$ straight or branched alkyl are substituted.

4. A method for preparing a compound represented by formula 1 comprising the following steps as shown in the below reaction formula 1:

preparing a compound represented by formula 3 by replacing the halogen (X) of a compound represented by formula 2 with piperazine (step 1); and preparing a compound represented by formula 1 by reacting the compound represented by formula 3 prepared in step 1) with a compound represented by formula 4 (step 2),

[Reaction Formula 1]

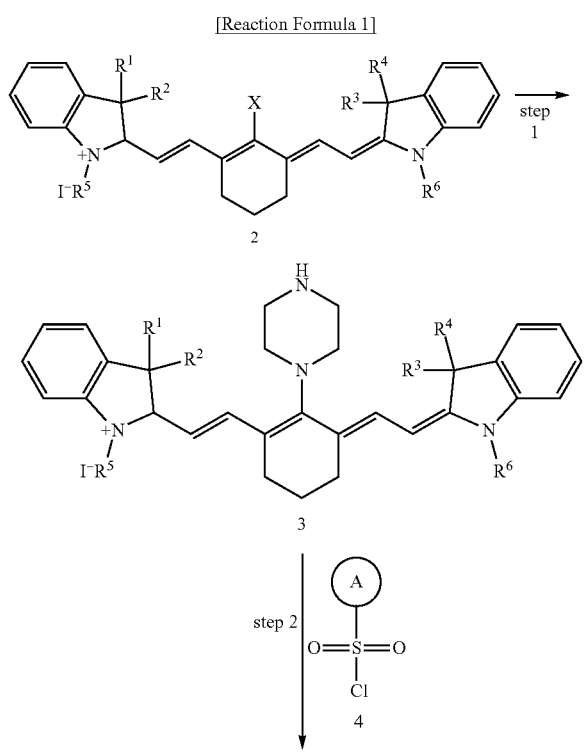

-continued

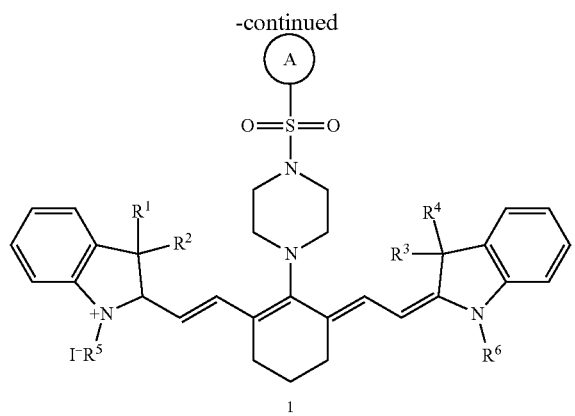

wherein,
X is halogen;

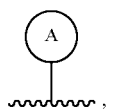

$R^1$, $R^2$, $R^3$, $R^4$, $R^5$, and $R^6$ are as defined in formula 1 of claim 1.

5. A method for detecting an amino acid containing thiol group comprising contacting the compound of claim 1 with a biosample.

6. The method for detecting an amino acid containing thiol group according to claim 5, wherein the amino acid containing thiol group is one or more amino acids selected from the group consisting of cysteine, homocysteine, and glutathione.

7. The method for detecting an amino acid containing thiol group according to claim 6, wherein the amino acid containing thiol group is glutathione.

8. A method for diagnosing a bacterial disease comprising contacting the compound of claim 1 with a biosample.

9. The method for diagnosing bacterial disease according to claim 8, wherein the bacterial disease is sepsis.

\* \* \* \* \*